(12) United States Patent
Kazarian et al.

(10) Patent No.: US 12,049,620 B2
(45) Date of Patent: Jul. 30, 2024

(54) PURIFICATION METHODS FOR GUANINE-RICH OLIGONUCLEOTIDES

(71) Applicant: AMGEN INC., Thousand Oaks, CA (US)

(72) Inventors: Artaches Kazarian, Belmont, MA (US); Wesley Barnhart, Newbury Park, CA (US); Iain David Grant Campuzano, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 812 days.

(21) Appl. No.: 17/275,115

(22) PCT Filed: Sep. 10, 2019

(86) PCT No.: PCT/US2019/050483
§ 371 (c)(1),
(2) Date: Mar. 10, 2021

(87) PCT Pub. No.: WO2020/055922
PCT Pub. Date: Mar. 19, 2020

(65) Prior Publication Data
US 2022/0049240 A1    Feb. 17, 2022

Related U.S. Application Data

(60) Provisional application No. 62/729,878, filed on Sep. 11, 2018.

(51) Int. Cl.
*B01D 15/16* (2006.01)
*B01D 15/36* (2006.01)
(Continued)

(52) U.S. Cl.
CPC ......... *C12N 15/101* (2013.01); *B01D 15/166* (2013.01); *B01D 15/363* (2013.01);
(Continued)

(58) Field of Classification Search
CPC ...... B01D 15/166; B01D 15/363; B01J 41/20; C12N 15/101; C12N 15/111; C12N 2310/321; C12N 2310/3231
See application file for complete search history.

(56) References Cited

U.S. PATENT DOCUMENTS

| | | | |
|---|---|---|---|
| 8,586,728 B2 * | 11/2013 | Sproat | C07H 1/06 536/25.3 |
| 8,877,725 B2 | 11/2014 | Iversen et al. | |
| 2005/0136458 A1 | 6/2005 | Dale et al. | |

FOREIGN PATENT DOCUMENTS

| | | |
|---|---|---|
| WO | 95/14087 A1 | 5/1995 |
| WO | 95/27718 A2 | 10/1995 |

(Continued)

OTHER PUBLICATIONS

Kazarian, A., et al., "Purification of guanine-quadruplex using monolithic stationary phase under ion-exchange conditions", Journal of Chromatography A, 1634, 461633, pp. 1-10. (Year: 2020).*

(Continued)

*Primary Examiner* — Benjamin L Lebron
(74) *Attorney, Agent, or Firm* — Angela L. Purcell

(57) ABSTRACT

The present invention relates to methods for purifying nucleic acids. In particular, the present invention relates to a method for separating guanine-rich oligonucleotides from quadruplex secondary structures formed from the oligonucleotides using monolithic anion exchange chromatography. Mobile phase parameters that control quadruplex formation and enable separation of the intact quadruplex from the single-strand oligonucleotide are also described.

43 Claims, 9 Drawing Sheets

Specification includes a Sequence Listing.

(51) Int. Cl.
*B01J 41/20* (2006.01)
*C12N 15/10* (2006.01)
*C12N 15/11* (2006.01)

(52) U.S. Cl.
CPC .............. *B01J 41/20* (2013.01); *C12N 15/111* (2013.01); *C12N 2310/321* (2013.01); *C12N 2310/3231* (2013.01)

(56) References Cited

FOREIGN PATENT DOCUMENTS

| WO | 01/27331 A2 | 4/2001 |
|---|---|---|
| WO | 03/080834 A2 | 10/2003 |
| WO | 2013/045434 A1 | 4/2013 |
| WO | 2014/144767 A1 | 9/2014 |

OTHER PUBLICATIONS

Bates et al. (2009), "Discovery and development of the G-rich oligonucleotide AS1411 as a novel treatment for cancer", Exper. Molec. Pathol., 86:151-164.

Burge et al. (2006), "Quadruplex DNA: sequence, topology and structure", Nucleic Acids Res., 34(19):5402-5415.

Nischang (2013), "Porous polymer monoliths: Morphology, porous properties, polymer nanoscale gel structure and their impact on chromatographic performance," J. Chromatography A, 1287:39-58.

Rhodes et al. (2015), "G-quadruplexes and their regulatory roles in biology", Nucleic Acids Res., 43(18):8627-8637.

Romanovskaya et al. (2013), "High-throughput purification of double-stranded RNA molecules using convective interaction media monolithic anion exchange columns," J. Chromatography A, 1278:54-60.

Svec (2004), "Preparation and HPLC applications of rigid macroporous organic polymer monoliths," J. Sep. Sci., 27:747-766.

Tam et al. (1999), "Increased potency of an aptameric G-rich oligonucleotide is associated with novel functional properties of phosphorothioate linkages", Antisense Nucleic Acid Drug Dev., 9(3):289-300.

Thayer et al. (2011), "Separation of oligonucleotide phosphorothioate diastereoisomers by pellicular anion-exchange chromatography", J. Chromatography A, 1218:802-808.

Wieder et al. (2006), "Monolithic poly(glycidyl methacrylate-co-divinylbenzene) capillary columns functionalized to strong anion exchangers for nucleotide and oligonucleotide separation", J. Separation Sci., 29(16):2478-2484.

Zimmermann et al. (2014), "Synthetic oligonucleotide separations by mixed-mode reversed-phase/weak anion-exchange liquid chromatography", J. Chromatography A, 1354:43-55.

Written Opinion and International Search Report for Appl. No. PCT/US2019/050483 mailed Dec. 18, 2019.

Santos et al., "Purification of supercoiled G-quadruplex pDNA for in vitro transcription," Separation and Purification Technology, vol. 163, pp. 59-71 (2016).

\* cited by examiner

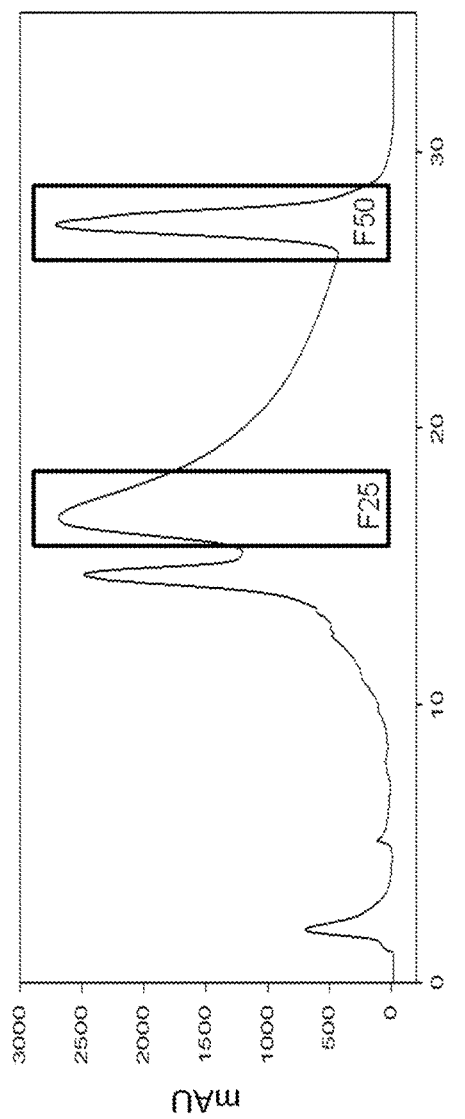
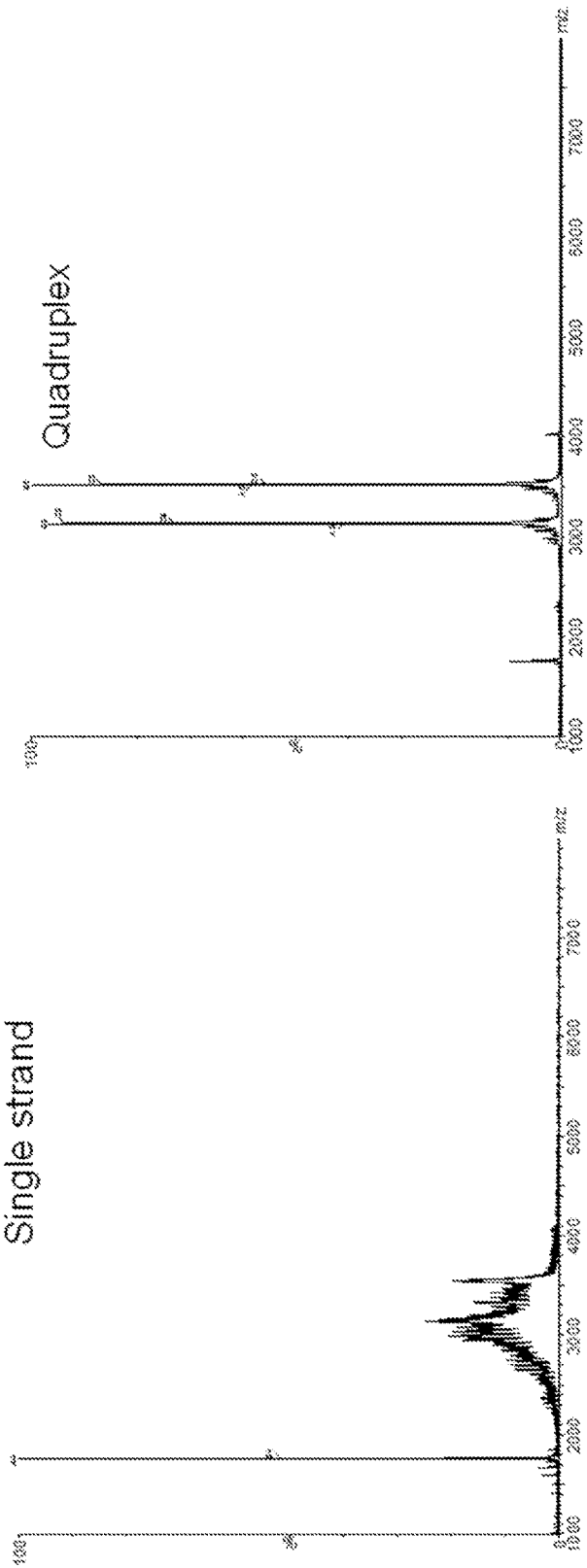
FIG. 5A
FIG. 5B
FIG. 5C

SEQUENCE LISTING

<160> NUMBER OF SEQ ID NOS: 1

<210> SEQ ID NO 1
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 1
ucguauaaca auaaggggcu g                    21

PURIFICATION METHODS FOR GUANINE-RICH OLIGONUCLEOTIDES

CROSS-REFERENCE TO RELATED APPLICATIONS

This application claims the benefit of U.S. Provisional Application No. 62/729,878, filed Sep. 11, 2018, which is hereby incorporated by reference in its entirety.

DESCRIPTION OF THE TEXT FILE SUBMITTED ELECTRONICALLY

The present application contains a Sequence Listing, which has been submitted electronically in ASCII format and is hereby incorporated by reference in its entirety. The computer readable format copy of the Sequence Listing, which was created on Sep. 6, 2019, is named A-2265-WO-PCT_SeqList_ST25 and is 527 bytes in size.

FIELD OF THE INVENTION

The present invention relates to the field of nucleic acid purification. In particular, the invention relates to methods for separating guanine-rich oligonucleotides from quadruplex secondary structures formed from the oligonucleotides using monolithic anion exchange chromatography. The methods allow for the purification of intact quadruplex as well as the single-strand guanine-rich oligonucleotide away from failure sequences and other impurities.

BACKGROUND OF THE INVENTION

Guanine-rich nucleic acids have long been known to self-associate to form four-stranded quadruplex secondary structures. See, e.g., Burge et al., Nucleic Acids Research, Vol. 34: 5402-5415, 2006 and Rhodes and Lipps, Nucleic Acids Research, Vol. 43: 8627-8637, 2015. In the last several years, there is increasing evidence that quadruplex structures are present in vivo and may play a role in various physiological functions, such as in DNA replication, telomere maintenance, and gene expression. See Rhodes and Lipps, 2015. To more fully understand the structure of the quadruplexes, their folding/unfolding kinetics, and their role in physiological processes, methods of isolating and purifying intact quadruplex structures is necessary.

Common practices for purification of synthetic nucleic acids typically utilize either reversed phase high performance liquid chromatography (RP-HPLC) or ion-exchange chromatography technologies with silica or polymer particle-based stationary phases. For RP-HPLC purification methods, a 5'-O-trityl protecting group is commonly used to protect the 5'-hydroxyl group of the synthetic oligonucleotide during synthesis and then used to purify the full-length oligonucleotides ("trityl on" sequences) from the shorter failure sequences that do not possess the 5'-O-trityl protecting group ("trityl off" sequences). However, such methods require additional steps to remove the trityl protecting group following purification adding to the cost and time of the overall purification. Large scale RP-HPLC purification procedures can also be costly due to the high use of organic solvents and the need for highly specialized equipment to handle elevated pressure requirements.

Ion-exchange chromatography has also been frequently used for purification of natural and synthetic oligonucleotides. Scale-up purification for ion exchange chromatography is significantly less costly than RP-HPLC methods and the pressure requirement is substantially lower. Oligonucleotides have been successfully separated using ion exchange chromatography both on an analytical and preparative scale. However, guanine-rich oligonucleotides that can form quadruplex secondary structures can exhibit extensive retention on, and in some cases irreversible binding to, the anion exchange stationary phase due to their bulky size and charge, thereby making purification of these guanine-rich oligonucleotides difficult or impossible by anion exchange chromatography.

Generally, most approaches for purifying guanine-rich oligonucleotides aim to disrupt secondary interactions, such as quadruplex formation, by using elevated temperatures, high pH buffers, or introducing chaotropic agents or organic modifiers. Such strongly denaturing conditions promote single-strand formation. The single strand could then be purified, but the quadruplex would then need to be assembled from the purified single strands.

Thus, there is a need in the art for efficient, scalable methods for separating single-strand guanine-rich oligonucleotides from intact quadruplex secondary structures.

SUMMARY OF THE INVENTION

The present invention is based, in part, on the discovery that quadruplex formation from guanine-rich oligonucleotides can be carefully controlled during anion exchange monolithic chromatography, thereby allowing the separation of single-strand guanine-rich oligonucleotide from the intact quadruplex. The method also allows both the single-strand guanine-rich oligonucleotide and the intact quadruplex to be separated from failure sequences and other impurities.

Accordingly, the present invention provides a method for separating a guanine-rich oligonucleotide from a quadruplex structure formed from the guanine-rich oligonucleotide. In one embodiment, the method comprises contacting a solution with a monolithic anion exchange matrix; passing a mobile phase described herein through the monolithic anion exchange matrix; and collecting elution fractions from the monolithic anion exchange matrix, wherein the guanine-rich oligonucleotide is eluted in one set of elution fractions and a quadruplex formed from the guanine-rich oligonucleotide is eluted in another set of elution fractions, thereby separating the oligonucleotide from the quadruplex.

In certain embodiments, the present invention also provides a method for purifying a guanine-rich oligonucleotide capable of forming a quadruplex structure from one or more impurities. In one embodiment, the method comprises contacting a solution comprising the oligonucleotide and one or more impurities with a monolithic anion exchange matrix; passing a mobile phase described herein through the monolithic anion exchange matrix; and collecting elution fractions from the monolithic anion exchange matrix, wherein one or more impurities are eluted in a first set of elution fractions, the guanine-rich oligonucleotide is eluted in a second set of elution fractions, and a quadruplex structure formed from the guanine-rich oligonucleotide is eluted in a third set of elution fractions, thereby separating the oligonucleotide from the impurities. In some embodiments, one or more impurities comprises one or more failure sequences.

The monolithic anion exchange matrix employed in the methods of the invention is generally comprised of a cross-linked polymer backbone to which positively-charged functional groups are covalently linked. In some embodiments, the cross-linked polymer backbone is a poly(glycidyl methacrylate-co-ethylene dimethacrylate) backbone or a poly(styrene-co-divinylbenzene) backbone. The positively-charged functional groups attached to the backbone in the monolithic anion exchange matrix can be a primary amine, a secondary amine, a tertiary amine, or a quaternary amine. In certain embodiments, the positively-charged functional group is selected from a quaternary amine, a polyethylenimine, a diethylaminomethyl, a diethylaminoethyl, a dimethylaminopropyl, an ethylendiamino, or a polyallylamine. Preferably, the monolithic anion exchange matrix used in the methods of the invention has a pore size of at least 200 nm. In some embodiments, the monolithic anion exchange matrix has a pore size of at least 500 nm, for example, from about 500 nm to about 2,000 nm. In one embodiment, the monolithic anion exchange matrix has a pore size from about 800 nm to about 1,500 nm. In another embodiment, the monolithic anion exchange matrix has a pore size from about 1,800 nm to about 2,200 nm. In yet another embodiment, the monolithic anion exchange matrix has a pore size from about 1,300 nm to about 2,000 nm.

The mobile phases used in the methods of the invention have a pH of about 7.0 to about 9.0 and comprise a buffer and an organic solvent. The buffer can be any buffer able to maintain the pH in the target range, such as sodium phosphate, Tris hydrochloride, HEPES, or MOPS, and can be present in a concentration of about 10 mM to about 200 mM. In one embodiment, the mobile phase comprises about 20 mM to about 100 mM of a buffer. Suitable organic solvents that can be used in the mobile phase include acetonitrile, methanol, propanol, isopropanol, ethanol, butanol, tetrahydrofuran, or acetone. In some embodiments, the organic solvent may be present in the mobile phase at a concentration of about 1% (v/v) to about 50% (v/v) or from about 1% (v/v) to about 20% (v/v).

The mobile phases used in the methods of the invention also comprise an elution salt, the concentration of which increases over the time period of the separation. The elution salt can be, for example, sodium salts, potassium salts, ammonium salts, trimethylammonium salts, triethylammonium salts, chloride salts, bromide salts, nitrate salts, nitrite salts, iodide salts, perchlorate salts, acetate salts, or formate salts. In certain embodiments, the elution salt is selected from sodium bromide, potassium bromide, ammonium bromide, sodium chloride, potassium chloride, and ammonium chloride. During the separation, the increase in concentration of the elution salt in the mobile phase can be a concentration gradient of the elution salt, for example from 0 M to 2 M or from 0 M to 1 M. The concentration gradient can be a linear gradient or a step gradient. In one embodiment, the mobile phase has a pH of about 7.5 to about 8.5 and comprises a sodium phosphate buffer, acetonitrile, and sodium bromide, where the concentration of the sodium bromide increases at a gradient of 0 M to 1 M in a stepwise manner (e.g. step gradient) over the course of the separation.

In certain embodiments, the methods further comprise isolating the elution fraction or set of elution fractions comprising the guanine-rich oligonucleotide and/or the elution fraction or set of elution fractions comprising the quadruplex. The isolated elution fractions can be subject to one or more further processing steps, such as one or more further purification steps (e.g. desalting), conjugation reactions to covalently attach a targeting ligand to the oligonucleotide, annealing reactions to hybridize the oligonucleotide with a complementary strand to form a double-stranded RNA interference agent, and formulation steps to prepare pharmaceutical compositions of the oligonucleotide for administration to patients for therapeutic purposes.

In some embodiments, the methods of the invention further comprise isolating the elution fraction or set of elution fractions comprising the quadruplex and subjecting the fraction(s) to denaturing conditions. The isolated quadruplex is comprised predominantly of the single-strand oligonucleotide and does not significantly trap failure sequences and other impurities. Therefore, highly purified preparations of the single-stranded guanine-rich oligonucleotide can be obtained by denaturing the quadruplex. In one embodiment, the denaturing conditions comprise heating the fraction(s) comprising the quadruplex to elevated temperatures sufficient to disrupt hydrogen bonding interactions, for example to a temperature from about 45° C. to about 95° C. In another embodiment, the denaturing conditions comprise increasing the pH of the fraction(s) comprising the quadruplex to strongly alkaline conditions, for example to a pH from about 9.5 to about 13. In yet another embodiment, the denaturing conditions comprise exposing the fraction(s) comprising the quadruplex to a chaotropic agent, such as urea. The purity of the guanine-rich oligonucleotide in solutions obtained from denaturing the quadruplex can be at least 85%. In some embodiments, the purity of the guanine-rich oligonucleotide in solutions obtained from denaturing the quadruplex is at least 88%. In other embodiments, the purity of the guanine-rich oligonucleotide in solutions obtained from denaturing the quadruplex is at least 90%.

The guanine-rich oligonucleotides that can be purified according to the methods of the invention can be naturally-occurring oligonucleotides, such as fragments of genomic DNA (e.g. telomere regions or promoter regions) or messenger RNA (e.g. untranslated regions), or they can be synthetic oligonucleotides. In some embodiments, the guanine-rich oligonucleotides to be purified according to the methods of the invention are therapeutic oligonucleotides designed to target a gene or RNA molecule associated with a disease or disorder. Such therapeutic oligonucleotides include a short hairpin RNA (shRNA), a precursor miRNA (pre-miRNA), an anti-miRNA oligonucleotide (e.g. antagomir and antimiR), an antisense oligonucleotide, a small interfering RNA (siRNA), a microRNA (miRNA), or a miRNA mimetic. In one embodiment, the guanine-rich oligonucleotide is an antisense oligonucleotide, wherein the antisense oligonucleotide comprises a nucleobase sequence complementary to a region of a target gene sequence having at least four consecutive cytosine bases. In another embodiment, the guanine-rich oligonucleotide is an antisense strand of an siRNA, wherein the antisense strand comprises a nucleobase sequence complementary to a region of a target gene sequence having at least four consecutive cytosine bases. The guanine-rich oligonucleotides that can be purified according to the methods of the invention may comprise one or more modified nucleotides, such as 2'-modified nucleotides and phosphorothioate internucleotide linkages.

BRIEF DESCRIPTION OF THE DRAWINGS

FIG. 5A shows a preparative chromatogram of the separation of a guanine-rich 21-mer oligonucleotide using an anion exchange monolithic column (CIM-QA-8 mL column). The oligonucleotide was loaded onto the column at 30 mg (1200 µL) and separated at a flow rate of 10 mL/min using a 20 mM $Na_2HPO_4$, 10% acetonitrile (v/v) mobile phase, pH 8.5 with elution by an increasing gradient of ammonium bromide. Detection was by UV absorbance at 260 nm. The threshold for fraction collection was set at 500 mAU. Fraction 25 (F25) containing the peak corresponding to the single-strand oligonucleotide and Fraction 50 (F50) containing the peak corresponding to the quadruplex were analyzed by native mass spectrometry.

FIG. 5B is a native mass spectrum of Fraction 25 from the preparative chromatographic purification shown in FIG. 5A. The predominant species in Fraction 25 is a peak corresponding to a molecular weight of about 7 kDa, which is the expected molecular weight for the single-strand oligonucleotide.

FIG. 5C is a native mass spectrum of Fraction 50 from the preparative chromatographic purification shown in FIG. 5A. Two primary peaks corresponding to a molecular weight of about 28 kDa are observed, which is the expected molecular weight for the intact quadruplex comprised of four strands of the guanine-rich oligonucleotide.

DETAILED DESCRIPTION

Figure 1:
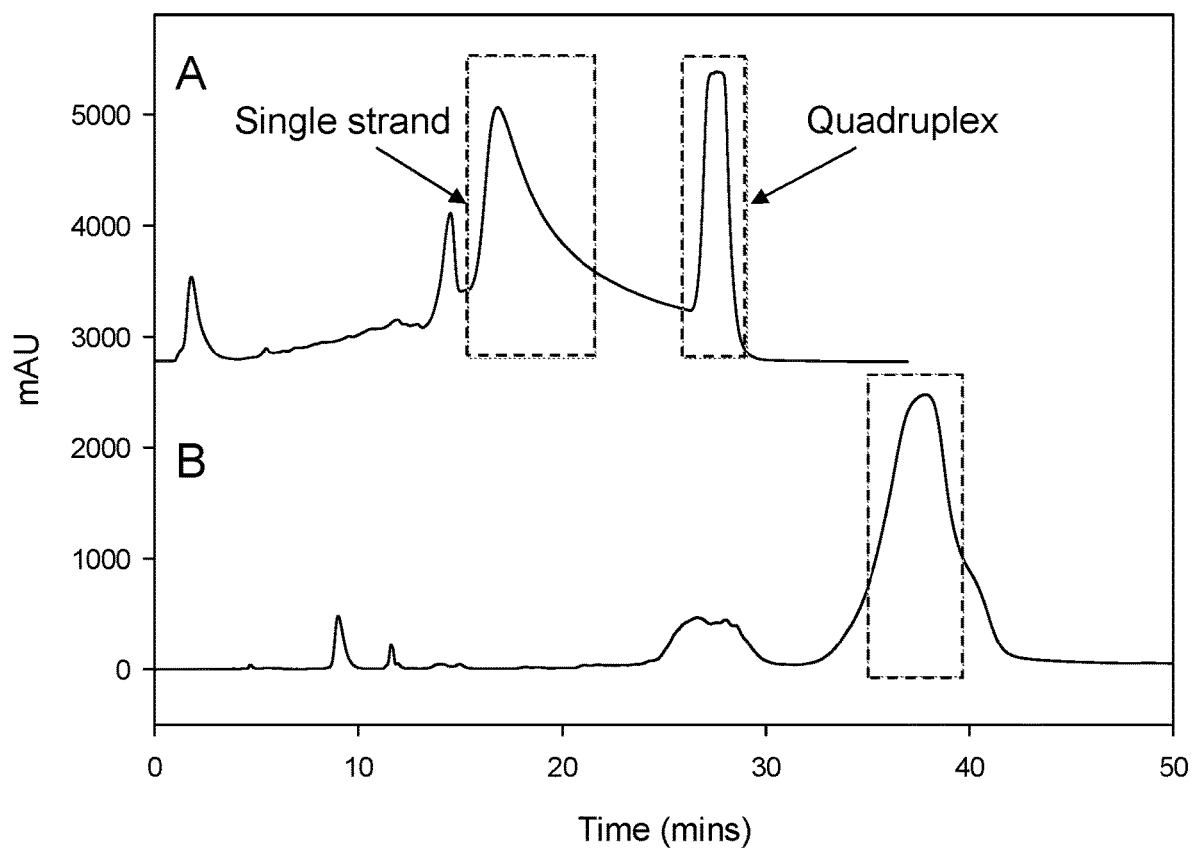
FIG. 1 depicts preparative chromatograms of the separation of a guanine-rich 21-mer oligonucleotide using an anion exchange monolithic column (CIM-QA-8 mL column; Trace A) or a polymer bead-based anion exchange resin (TSK-gel SuperQ-5PW column; Trace B). A solution comprising the oligonucleotide was separated either on an anion-exchange monolithic column (CIM-QA-8 mL) at a flow rate of 10 mL/min or on a column packed with a polymer bead-based anion exchange resin (TSK-gel SuperQ-5PW) at a flow rate of 8 mL/min using a 20 mM $Na_2HPO_4$, 10% acetonitrile (v/v) mobile phase, pH 8.5 with elution by an increasing gradient of sodium bromide. Detection was by UV absorbance at 260 nm.

The present invention relates to a preparative purification method for guanine-rich oligonucleotides that have a tendency to form quadruplex secondary structures. The invention is based, in part, on the discovery that the formation of quadruplex secondary structures from the guanine-rich oligonucleotides can be carefully controlled during anion exchange monolithic chromatography by adjusting the chromatographic operating conditions, thereby allowing resolution between the single-strand oligonucleotides and the intact quadruplex secondary structures.

The present inventors have surprisingly found that by inducing formation of the quadruplex more slowly during chromatographic separation, the quadruplex can be separated away from the single-strand oligonucleotide as well as failure sequences and other impurities. It has been reported in the literature that the confinement effect can contribute to the rapid formation and stabilization of quadruplex structures (Shrestha et al., Nat. Nanotechnol, Vol. 12: 582-588, 2017). Without being bound by theory, the present inventors believe that the large pore sizes of the monolithic stationary phase decrease the confinement effect, thereby slowing the formation of the quadruplex. By adjusting the composition of the mobile phase during separation with the monolithic stationary phase, quadruplex formation can be carefully controlled such that the resulting quadruplex structure is predominantly comprised of the guanine-rich oligonucleotides and does not trap failure sequences or other impurities. The intact quadruplex can be isolated and optionally denatured to obtain highly pure preparations of the single-strand guanine-rich oligonucleotides. Accordingly, the present invention provides methods for separating a guanine-rich oligonucleotide from a quadruplex structure formed from the guanine-rich oligonucleotide and one or more impurities comprising: contacting a solution comprising the oligonucleotide and one or more impurities with a monolithic anion exchange matrix; passing a mobile phase through the monolithic anion exchange matrix, wherein the mobile phase has a pH of about 7.0 to about 9.0 and comprises a buffer, an organic solvent, and an elution salt, wherein the concentration of the elution salt in the mobile phase increases over time; and collecting elution fractions from the monolithic anion exchange matrix, wherein one or more impurities are eluted in a first set of elution fractions, the guanine-rich oligonucleotide is eluted in a second set of elution fractions, and a quadruplex structure formed from the guanine-rich oligonucleotide is eluted in a third set of elution fractions. The methods of the invention provide purification of intact quadruplex structure and single-strand guanine-rich oligonucleotides on a preparative scale and the methods can readily be scaled up to produce commercial scale amounts of highly purified single-strand guanine-rich oligonucleotides and quadruplexes.

A guanine-rich oligonucleotide to be purified according to the methods of the invention is an oligonucleotide comprising at least one sequence motif of three or more consecutive guanine bases. Oligonucleotides containing such sequence motifs (also referred to as G-tracts) separated by other bases have been observed to spontaneously fold into quadruplex (also referred to as G-quadruplex or tetraplex) secondary structures. See, e.g., Burge et al., Nucleic Acids Research, Vol. 34: 5402-5415, 2006 and Rhodes and Lipps, Nucleic Acids Research, Vol. 43: 8627-8637, 2015. Quadruplexes are four-stranded helical structures that are assembled from planar G-quartets that are formed from the association of four guanine bases into a cyclic arrangement stabilized by Hoogsteen hydrogen bonding. The G-quartets can stack on top of each other to form the four-stranded helical quadruplex structure. See Burge et al., 2006 and Rhodes and Lipps, 2015. Quadruplexes can be formed from intramolecular or intermolecular folding of guanine-rich oligonucleotides depending on the number of G-tracts (i.e. sequence motifs of three or more consecutive guanine bases) present in the oligonucleotides. For example, quadruplexes can be formed from the intramolecular folding of a single oligonucleotide comprising four or more G-tracts. Alternatively, quadruplexes can be formed from the intermolecular folding of two oligonucleotides comprising at least two G-tracts or four oligonucleotides comprising at least one G-tract. See Burge et al., 2006 and Rhodes and Lipps, 2015.

In certain embodiments, the guanine-rich oligonucleotide to be purified according to the methods of the invention has at least one sequence motif of three consecutive guanine bases. In other embodiments, the guanine-rich oligonucleotide has at least one sequence motif of four consecutive guanine bases. In yet other embodiments, the guanine-rich oligonucleotide has a single sequence motif of three consecutive guanine bases. In still other embodiments, the guanine-rich oligonucleotide has a single sequence motif of four consecutive guanine bases. In some embodiments, the guanine-rich oligonucleotide has a sequence of at least four consecutive guanine bases. The guanine-rich oligonucleotide to be purified according to the methods of the invention may contain a quadruplex-forming consensus sequence, such as those found in telomeres or certain promoter regions. For instance, in one embodiment, the guanine-rich oligonucleotide may comprise a sequence motif of TTAGGG. In another embodiment, the guanine-rich oligonucleotide may comprise a sequence motif of GGGGCC. In another embodiment, the guanine-rich oligonucleotide may comprise a sequence motif of $(G_pN_q)_n$, where G is a guanine base, N is any nucleobase, p is at least 3, q is 1-7, and n is 1-4. In certain embodiments, p is 3 or 4.

As used herein, an oligonucleotide refers to an oligomer or polymer of nucleotides. The oligonucleotide may comprise ribonucleotides, deoxyribonucleotides, modified nucleotides, or combinations thereof. Oligonucleotides can be a few nucleotides in length up to several hundred nucleotides in length, for example, from about 10 nucleotides in length to about 300 nucleotides in length, from about 12 nucleotides in length to about 100 nucleotides in length, from about 15 nucleotides in length to about 250 nucleotides in length, from about 20 nucleotides in length to about 80 nucleotides in length, from about 15 nucleotides in length to about 30 nucleotides in length, or from about 18 nucleotides in length to about 26 nucleotides in length. In some embodiments, the guanine-rich oligonucleotide to be purified according to the methods of the invention is about 18, 19, 20, 21, 22, 23, 24, 25, or 26 nucleotides in length. In one embodiment, the guanine-rich oligonucleotide is about 19 nucleotides in length. In another embodiment, the guanine-rich oligonucleotide is about 20 nucleotides in length. In yet another embodiment, the guanine-rich oligonucleotide is about 21 nucleotides in length. In still another embodiment, the guanine-rich oligonucleotide is about 23 nucleotides in length.

The guanine-rich oligonucleotide may be a naturally-occurring oligonucleotide isolated from a cell or organism. For instance, the guanine-rich oligonucleotide may be derived from or a fragment of genomic DNA, particularly the telomere or promoter regions, or may be derived from or a fragment of messenger RNA (mRNA), particularly the 5' or 3' untranslated regions. In some embodiments, the guanine-rich oligonucleotide is a synthetic oligonucleotide produced by chemical synthetic methods or in vitro enzymatic methods. In some embodiments, the guanine-rich oligonucleotide can be a short hairpin RNA (shRNA), a precursor miRNA (pre-miRNA), an anti-miRNA oligonucleotide (e.g. antagomir and antimiR), or an antisense oligonucleotide. In other embodiments, the guanine-rich oligonucleotide can be one of the component strands of a double-stranded RNA molecule or RNA interference agent, such as a small interfering RNA (siRNA), a microRNA (miRNA), or a miRNA mimetic.

In certain embodiments, the guanine-rich oligonucleotide is a therapeutic oligonucleotide designed to target a gene or RNA molecule associated with a disease or disorder. For instance, in one embodiment, the guanine-rich oligonucleotide is an antisense oligonucleotide that comprises a sequence complementary to a region of a target gene or mRNA sequence having at least three or at least four consecutive cytosine bases. A first sequence is "complementary" to a second sequence if an oligonucleotide comprising the first sequence can hybridize to an oligonucleotide comprising the second sequence to form a duplex region under certain conditions. "Hybridize" or "hybridization" refers to the pairing of complementary oligonucleotides, typically via hydrogen bonding (e.g. Watson-Crick, Hoogsteen or reverse Hoogsteen hydrogen bonding) between complementary bases in the two oligonucleotides. A first sequence is considered to be fully complementary (100% complementary) to a second sequence if an oligonucleotide comprising the first sequence base pairs with an oligonucleotide comprising the second sequence over the entire length of one or both nucleotide sequences without any mismatches.

In another embodiment, the guanine-rich oligonucleotide is an antisense strand of an siRNA or other type of double-stranded RNA interference agent, wherein the antisense strand comprises a sequence that is complementary to a region of a target gene or mRNA sequence having at least three or at least four consecutive cytosine bases. In yet another embodiment, the guanine-rich oligonucleotide is a sense strand of an siRNA or other type of double-stranded RNA interference agent, wherein the sense strand comprises a sequence identical to a region of a target gene or mRNA sequence having at least three or at least four consecutive guanine bases. The strand of an siRNA or other type of double-stranded RNA interference agent comprising a region having a sequence that is complementary to a target sequence (e.g. target mRNA) is referred to as the "antisense strand." The "sense strand" refers to the strand that includes a region that is complementary to a region of the antisense strand.

The guanine-rich oligonucleotide to be purified according to the methods of the invention may comprise one or more modified nucleotides. A "modified nucleotide" refers to a nucleotide that has one or more chemical modifications to the nucleoside, nucleobase, pentose ring, or phosphate group. Such modified nucleotides can include, but are not limited to, nucleotides with 2' sugar modifications (2'-O-methyl, 2'-methoxyethyl, 2'-fluoro, etc.), abasic nucleotides, inverted nucleotides (3'-3' linked nucleotides), phosphorothioate linked nucleotides, nucleotides with bicyclic sugar modifications (e.g. LNA, ENA), and nucleotides comprising base analogs (e.g. universal bases, 5-methylcytosine, pseudouracil, etc.).

In certain embodiments, the modified nucleotides have a modification of the ribose sugar. These sugar modifications can include modifications at the 2' and/or 5' position of the pentose ring as well as bicyclic sugar modifications. A 2'-modified nucleotide refers to a nucleotide having a pentose ring with a substituent at the 2' position other than H or OH. Such 2'-modifications include, but are not limited to, 2'-O-alkyl (e.g. O—$C_1$-$C_{10}$ or O—$C_1$-$C_{10}$ substituted alkyl), 2'-O-allyl (O—$CH_2CH$=$CH_2$), 2'-C-allyl, 2'-fluoro, 2'-O-methyl ($OCH_3$), 2'-O-methoxyethyl (O—$(CH_2)_2OCH_3$), 2'-$OCF_3$, 2'-O$(CH_2)_2SCH_3$, 2'-O-aminoalkyl, 2'-amino (e.g. $NH_2$), 2'-O-ethylamine, and 2'-azido. Modifications at the 5' position of the pentose ring include, but are not limited to, 5'-methyl (R or S); 5'-vinyl, and 5'-methoxy. A "bicyclic sugar modification" refers to a modification of the pentose ring where a bridge connects two atoms of the ring to form a second ring resulting in a bicyclic sugar structure. In some embodiments the bicyclic sugar modification comprises a bridge between the 4' and 2' carbons of the pentose ring. Nucleotides comprising a sugar moiety with a bicyclic sugar modification are referred to herein as bicyclic nucleic acids or BNAs. Exemplary bicyclic sugar modifications include, but are not limited to, α-L-Methyleneoxy (4'-$CH_2$—O-2') bicyclic nucleic acid (BNA); β-D-Methyleneoxy (4'-$CH_2$—O-2') BNA (also referred to as a locked nucleic acid or LNA); Ethyleneoxy (4'-$(CH_2)_2$—O-2') BNA; Aminooxy (4'-$CH_2$-0 N(R)-2') BNA; Oxyamino (4'-$CH_2$—N(R)—O-2') BNA; Methyl(methyleneoxy) (4'-$CH(CH_3)$—O-2') BNA (also referred to as constrained ethyl or cEt); methylene-thio (4'-$CH_2$—S-2') BNA; methylene-amino (4'-$CH_2$—N(R)-2') BNA; methyl carbocyclic (4'-$CH_2$—$CH(CH_3)$-2') BNA; propylene carbocyclic (4'-$(CH_2)_3$-2') BNA; and Methoxy (ethyleneoxy) (4'-$CH(CH_2OMe)$-O-2') BNA (also referred to as constrained MOE or cMOE). These and other sugar-modified nucleotides that can be incorporated into guanine-rich oligonculeotide are described in U.S. Pat. No. 9,181,551, U.S. Patent Publication No. 2016/0122761, and Deleavey and Damha, Chemistry and Biology, Vol. 19: 937-954, 2012, all of which are hereby incorporated by reference in their entireties.

In some embodiments, the guanine-rich oligonucleotides comprise one or more 2'-fluoro modified nucleotides, 2'-O-methyl modified nucleotides, 2'-O-methoxyethyl modified nucleotides, 2'-O-allyl modified nucleotides, bicyclic nucleic acids (BNAs), or combinations thereof. In certain embodiments, the guanine-rich oligonucleotides comprise one or more 2'-fluoro modified nucleotides, 2'-O-methyl modified nucleotides, 2'-O-methoxyethyl modified nucleotides, or combinations thereof. In one particular embodiment, the guanine-rich oligonucleotides comprise one or more 2'-fluoro modified nucleotides, 2'-O-methyl modified nucleotides or combinations thereof.

The guanine-rich oligonucleotides that can be purified according to the methods of the invention may also comprise one or more modified internucleotide linkages. As used herein, the term "modified internucleotide linkage" refers to an internucleotide linkage other than the natural 3' to 5' phosphodiester linkage. In some embodiments, the modified internucleotide linkage is a phosphorous-containing internucleotide linkage, such as a phosphotriester, aminoalkylphosphotriester, an alkylphosphonate (e.g. methylphosphonate, 3'-alkylene phosphonate), a phosphinate, a phosphoramidate (e.g. 3'-amino phosphoramidate and aminoalkylphosphoramidate), a phosphorothioate (P=S), a chiral phosphorothioate, a phosphorodithioate, a thionophosphoramidate, a thionoalkylphosphonate, a thionoalkylphosphotriester, and a boranophosphate. In one embodiment, a modified internucleotide linkage is a 2' to 5' phosphodiester linkage. In other embodiments, the modified internucleotide linkage is a non-phosphorous-containing internucleotide linkage and thus can be referred to as a modified internucleoside linkage. Such non-phosphorous-containing linkages include, but are not limited to, morpholino linkages (formed in part from the sugar portion of a nucleoside); siloxane linkages (—O—Si(H)$_2$—O—); sulfide, sulfoxide and sulfone linkages; formacetyl and thioformacetyl linkages; alkene containing backbones; sulfamate backbones; methylenemethylimino (—$CH_2$—N($CH_3$)—O—$CH_2$—) and methylenehydrazino linkages; sulfonate and sulfonamide linkages; amide linkages; and others having mixed N, O, S and $CH_2$ component parts. In one embodiment, the modified internucleoside linkage is a peptide-based linkage (e.g. aminoethylglycine) to create a peptide nucleic acid or PNA, such as those described in U.S. Pat. Nos. 5,539,082; 5,714,331; and 5,719,262. Other suitable modified internucleotide and internucleoside linkages that may be incorporated into the guanine-rich oligonucleotides are described in U.S. Pat. Nos. 6,693,187, 9,181,551, U.S. Patent Publication No. 2016/0122761, and Deleavey and Damha, Chemistry and Biology, Vol. 19: 937-954, 2012, all of which are hereby incorporated by reference in their entireties.

In certain embodiments, the guanine-rich oligonucleotides comprise one or more phosphorothioate internucleotide linkages. The guanine-rich oligonucleotides may comprise 1, 2, 3, 4, 5, 6, 7, 8, or more phosphorothioate internucleotide linkages. In some embodiments, all of the internucleotide linkages in the guanine-rich oligonucleotides are phosphorothioate internucleotide linkages. In other embodiments, the guanine-rich oligonucleotides can comprise one or more phosphorothioate internucleotide linkages at the 3'-end, the 5'-end, or both the 3'- and 5'-ends. For instance, in certain embodiments, the guanine-rich oligonucleotides comprise about 1 to about 6 or more (e.g., about 1, 2, 3, 4, 5, 6 or more) consecutive phosphorothioate internucleotide linkages at the 3'-end. In other embodiments, the guanine-rich oligonucleotides comprise about 1 to about 6 or more (e.g., about 1, 2, 3, 4, 5, 6 or more) consecutive phosphorothioate internucleotide linkages at the 5'-end.

The guanine-rich oligonucleotides to be purified according to the methods of the invention can readily be made using techniques known in the art, for example, using conventional nucleic acid solid phase synthesis. The oligonucleotides can be assembled on a suitable nucleic acid synthesizer utilizing standard nucleotide or nucleoside precursors (e.g. phosphoramidites). Automated nucleic acid synthesizers are sold commercially by several vendors, including DNA/RNA synthesizers from Applied Biosystems (Foster City, CA), MerMade synthesizers from BioAutomation (Irving, TX), and OligoPilot synthesizers from GE Healthcare Life Sciences (Pittsburgh, PA). The 2' silyl protecting group can be used in conjunction with acid labile dimethoxytrityl (DMT) at the 5' position of ribonucleosides to synthesize oligonucleotides via phosphoramidite chemistry. Final deprotection conditions are known not to significantly degrade RNA products. All syntheses can be conducted in any automated or manual synthesizer on large, medium, or small scale. The syntheses may also be carried out in multiple well plates, columns, or glass slides. The 2'-O-silyl group can be removed via exposure to fluoride ions, which can include any source of fluoride ion, e.g., those salts containing fluoride ion paired with inorganic counterions e.g., cesium fluoride and potassium fluoride or those salts containing fluoride ion paired with an organic counterion, e.g., a tetraalkylammonium fluoride. A crown ether catalyst can be utilized in combination with the inorganic fluoride in the deprotection reaction. Preferred fluoride ion sources are tetrabutylammonium fluoride or aminohydrofluorides (e.g., combining aqueous HF with triethylamine in a dipolar aprotic solvent, e.g., dimethylformamide). The various synthetic steps may be performed in an alternate sequence or order to give the desired compounds. Other synthetic chemistry transformations, protecting groups (e.g., for hydroxyl, amino, etc. present on the bases) and protecting group methodologies (protection and deprotection) useful in synthesizing oligonucleotides are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

As can be appreciated by the skilled artisan, further methods of synthesizing the guanine-rich oligonucleotides will be evident to those of ordinary skill in the art. For instance, the oligonucleotides can be synthesized using enzymes in in vitro systems, such as in the methods described in Jensen and Davis, Biochemistry, Vol. 57: 1821-1832, 2018. Naturally-occurring oligonucleotides can be isolated from cells or organisms using conventional methods. Custom synthesis of oligonucleotides is also available from several commercial vendors, including Dharmacon, Inc. (Lafayette, CO), AxoLabs GmbH (Kulmbach, Germany), and Ambion, Inc. (Foster City, CA).

The methods of the invention can be used to purify or separate guanine-rich oligonucleotides or quadruplex structures from one or more impurities in a solution. "Purify" or "purification" refers to a process that reduces the amounts of substances that are different than the target molecule (e.g. guanine-rich oligonucleotide or quadruplex) and are desirably excluded from the final composition or preparation. The term "impurity" refers to a substance having a different structure than the target molecule and the term can include a single undesired substance or a combination of several undesired substances. Impurities can include materials or reagents used in the methods to produce the guanine-rich oligonucleotides as well as fragments or other undesirable derivatives or forms of the oligonucleotides. In certain embodiments, the impurities comprise one or more oligonucleotides having a shorter length than the target guanine-rich oligonucleotide. In these and other embodiments, the impurities comprise one or more failure sequences. Failure sequences can be generated during the synthesis of the target oligonucleotide and arise from the failure of coupling reactions during the stepwise addition of a nucleotide monomer to the oligonucleotide chain. The product of an oligonucleotide synthetic reaction is often a heterogeneous mixture of oligonucleotides of varying lengths comprising the target oligonucleotide and various failure sequences having lengths shorter than the target oligonucleotide (i.e. truncated versions of the target oligonucleotide). In some embodiments, the impurities comprise one or more process-related impurities. Depending on the synthetic method to produce the guanine-rich oligonucleotide, such process-related impurities can include, but are not limited to, nucleotide monomers, protecting groups, salts, enzymes, and endotoxins.

A solution from which a guanine-rich oligonucleotide can be purified can be any solution containing the oligonucleotide and one or more impurities or contaminants, the presence of which is not desired. A solution comprising the guanine-rich oligonucleotide and one or more impurities can include mixtures resulting from synthetic methods to produce the oligonucleotide. For example, in one embodiment the solution comprising the guanine-rich oligonucleotide and one or more impurities is a reaction mixture from a chemical synthetic method to produce the oligonucleotide, such as a synthetic reaction mixture obtained from an automated synthesizer. In such an embodiment, the solution may also comprise failure sequences. In another embodiment, the solution comprising the guanine-rich oligonucleotide and one or more impurities is a mixture from an in vitro enzymatic synthetic reaction (e.g. polymerase chain reaction (PCR)). In yet another embodiment, the solution comprising the guanine-rich oligonucleotide and one or more impurities is a cell lysate or biological sample, for example when the guanine-rich oligonucleotide is a naturally-occurring oligonucleotide isolated from a cell or organism. In still another embodiment, the solution comprising the guanine-rich oligonucleotide and one or more impurities is a solution or mixture from another purification operation, such as the eluate from a chromatographic separation.

In some embodiments, the solution from which a guanine-rich oligonucleotide is to be purified comprises from about 10 mg to about 50 mg of the guanine-rich oligonucleotide, from about 10 mg to about 30 mg of the guanine-rich oligonucleotide, or about 30 mg of the guanine-rich oligonucleotide. These load amounts are suitable for a monolithic column with a bed volume of 8 mL. Load amounts can be scaled up proportionally for monolithic columns with larger bed volumes as known by those of skill in the art. For instance, load amounts of the guanine-rich oligonucleotide for monolithic columns having a 10-fold larger bed volume could be 10-fold higher than the ranges described here. By way of example only, suitable load amounts of the guanine-rich oligonucleotide for a monolithic column having a bed volume of 80 mL could be from about 100 mg to about 500 mg.

The methods of the invention entail contacting the solution comprising the guanine-rich oligonucleotide to be purified with a monolithic anion exchange matrix. A monolithic anion exchange matrix refers to a porous material comprised of a single continuous structure of fused globules comprising positively-charged functional groups. Monolithic materials are generally comprised of cross-linked inorganic or organic polymers making up a backbone to which various chemical functional groups can be covalently attached. In certain embodiments, the monolithic anion exchange matrix used in the methods of the invention comprises a cross-linked organic polymer, such as poly(glycidyl methacrylate-co-ethylene dimethacrylate), to which positively-charged functional groups are covalently linked. Suitable organic polymers for generating the backbone of the monolithic anion exchange matrix include, but are not limited to, poly(glycidyl methacrylate-co-ethylene dimethacrylate), poly(styrene-co-divinylbenzene), poly(glycidyl methacrylate-co-trimethylolpropane trimethacrylate), poly(chloromethylstyrene-co-divinylbenzene), poly(butyl methacrylate-co-ethylene dimethacrylate), poly(p-methylstyrene-co-1,2-(4-vinylphenyl)ethane), and poly(lauryl methacrylate-co-ethylene dimethacrylate). Exemplary monomers and cross-linking agents as well as polymerization methods that can be used to produce the cross-linked polymer backbone of the monolithic anion exchange matrix are known in the art, such as those described, for example, in Svec, J. Sep. Sci., Vol. 27: 747-766, 2004 and Svec, J. Chromatogr. A., Vol. 1217: 902-924, 2010. In one embodiment, the monolithic anion exchange matrix employed in the methods of the invention comprises a poly(glycidyl methacrylate-co-ethylene dimethacrylate) backbone. In another embodiment, the monolithic anion exchange matrix used in the methods of the invention comprises a poly(styrene-co-divinylbenzene) backbone.

Preferably, the pore size of the monolithic anion exchange matrix is at least about 200 nm. For instance, the pore size of the monolithic anion exchange matrix can be from about 200 nm to about 10,000 nm, from about 400 nm to about 8,000 nm, from about 500 nm to about 5,000 nm, from about 1,000 nm to about 6,000 nm, from about 500 nm to about 2,000 nm, from about 1,000 nm to about 3,000 nm, from about 1,500 nm to about 4,000 nm, from about 800 nm to about 1,500 nm, from about 1,800 nm to about 2,200 nm, from about 1,300 nm to about 2,000 nm, or from about 600 nm to about 1,000 nm. In some embodiments, the pore size of the monolithic anion exchange matrix is at least 500 nm. In certain embodiments, the monolithic anion exchange matrix has a pore size from about 500 nm to about 2,000 nm. In other embodiments, the monolithic anion exchange matrix has a pore size from about 800 nm to about 1,500 nm. In yet other embodiments, the monolithic anion exchange matrix has a pore size from about 1,800 nm to about 2,200 nm. In one particular embodiment, the monolithic anion exchange matrix has a pore size of about 1,300 nm. In another particular embodiment, the monolithic anion exchange matrix has a pore size of about 2,000 nm. The pore size of monolithic supports can be controlled during the polymerization process by the choice and concentration of the porogenic solvent and the polymerization conditions. See, e.g., Svec, J. Sep. Sci., Vol. 27: 747-766, 2004 and Svec, J. Chromatogr. A., Vol. 1217: 902-924, 2010, and references cited therein.

The monolithic anion exchange matrix used in the methods of the invention will generally comprise positively-charged functional groups to enable the binding of negatively-charged molecules, such as oligonucleotides, to the monolithic matrix. The positively-charged functional groups can be a primary amine, a secondary amine, a tertiary amine, or a quaternary amine. In some embodiments, the positively-charged functional group in the monolithic anion exchange matrix is a strong anion exchange group, such as a quaternary amine. Strong anion exchange groups show no variation in ion exchange capacity with changes in pH and are fully charged at pH values between 2 and 13. In other embodiments, the positively-charged functional group in the monolithic anion exchange matrix is a weak anion exchange group, such as diethylaminoethyl and dimethylaminopropyl. Weak anion exchange groups are ionized only over a limited pH range (e.g. pH 3-9). The monolithic anion exchange matrix may comprise a positively-charged functional group selected from a quaternary amine, a polyethylenimine, a diethylaminomethyl, a diethylaminoethyl, a dimethylaminopropyl, an ethylendiamino, or a polyallylamine. In one embodiment, the monolithic anion exchange matrix comprises a quaternary amine group. In another embodiment, the monolithic anion exchange matrix comprises a diethylaminoethyl group. Methods of covalently attaching the positively-charged functional groups to the polymer backbone of the monolith are known in the art and can include reaction with or functionalization of the monomer units to create the polymer backbone. See, e.g., Svec, J. Sep. Sci., Vol. 27: 747-766, 2004 and Svec, J. Chromatogr. A., Vol. 1217: 902-924, 2010. Monolithic anion exchange matrices suitable for use in the methods of the invention are also available commercially, such as the Convective Interaction Media (CIM) line of columns available from BIA Separations, including the CIMmultus™ QA and CIMmultus™ DEAE columns.

Once the solution comprising the guanine-rich oligonucleotide and one or more impurities is contacted with the monolithic anion exchange matrix, a mobile phase is passed through the monolithic anion exchange matrix to carry the components of the solution through the matrix thereby allowing the components to interact to varying degrees with the positively-charged functional groups present in the matrix. As described in Example 2 herein, the composition of the mobile phase during the separation was optimized to carefully control the formation of the quadruplex structure and allow its separation away from single-stranded guanine-rich oligonucleotides and impurities, such as failure sequences.

The mobile phase used in the methods of the invention is typically a buffered solution at a pH of about 7.0 to about 9.0. In some embodiments, the pH of the mobile phase is about 7.5 to about 8.5. In other embodiments, the pH of the mobile phase is about 8.0 to about 8.5. In certain other embodiments, the pH of the mobile phase is about 8.3 to about 8.7. In one particular embodiment, the pH of the mobile phase is about 8.5. Any buffer can be used provided that the buffer is capable of maintaining the pH of the solution in the target pH range. Suitable buffers that buffer in this pH range that can be used as components of the mobile phase in the methods of the invention include, but are not limited to, HEPES (N-[2-hydroxyethyl]piperazine-N'-[2-ethanesulfonic acid]), Tris hydrochloride, phosphate, BES (N,N-bis[2-hydroxyethyl]-2-aminoethanesulfonic acid), Tricine (N-tris[hydroxymethyl]methylglycine), Bicine (N,N-Bis(2-hydroxyethyl)glycine), TES (N-tris[hydroxymethyl]methyl-2-aminoethanesulfonic acid), TAPSO (3-[N-Tris(hydroxymethyl)methylamino]-2-hydroxypropanesulfonic acid), PIPES (piperazine-N,N'-bis(2-ethanesulfonic acid)), Bis-Tris (Bis(2-hydroxyethyl)amino-tris(hydroxymethyl)methane), and MOPS (3-[N-morpholino] propanesulfonic acid). In certain embodiments, the mobile phase comprises a buffer selected from sodium phosphate, Tris hydrochloride, HEPES, or MOPS. The buffer can be present in a concentration from about 10 mM to about 200 mM, from about 15 mM to about 150 mM, from about 20 mM to about 100 mM, from about 25 mM to about 75 mM, or from about 15 mM to about 25 mM. In some embodiments, the mobile phase comprises a sodium phosphate buffer, for example in a concentration of about 20 mM to about 100 mM. In other embodiments, the mobile phase comprises a HEPES buffer, for example in a concentration of about 20 mM to about 100 mM. In certain other embodiments, the mobile phase comprises a Tris buffer, for example in a concentration of about 20 mM to about 100 mM. In still other embodiments, the mobile phase comprises a MOPS buffer, for example in a concentration of about 20 mM to about 100 mM.

In certain embodiments, the mobile phase comprises an organic solvent. Exemplary organic solvents that can be included in the mobile phase include, but are not limited to, acetonitrile, methanol, propanol, isopropanol, ethanol, butanol, tetrahydrofuran, and acetone. In some embodiments, the organic solvent is methanol, acetonitrile, or tetrahydrofuran. In one embodiment, the organic solvent is acetonitrile. In another embodiment, the organic solvent is methanol. The organic solvent can be present in the mobile phase at a concentration between about 0% (v/v) and 100% (v/v) depending on the nature of the molecules to be separated. For instance, higher concentrations of organic solvent may be used to purify more hydrophobic oligonucleotides and ensure they are desorbed from the monolithic anion exchange matrix. The concentration of the organic solvent in the mobile phase can be from about 1% (v/v) to about 50% (v/v), from about 1% (v/v) to about 20% (v/v), from about 15% (v/v) to about 35% (v/v), from about 30% (v/v) to about 60% (v/v), from about 55% (v/v) to about 75% (v/v), from about 70% (v/v) to about 100% (v/v), from about 5% (v/v) to about 15% (v/v), from about 5% (v/v) to about 25% (v/v), from about 1% (v/v) to about 10% (v/v), or from about 8% (v/v) to about 12% (v/v). In one embodiment, the organic solvent is present in the mobile phase at a concentration of about 10% (v/v). In another embodiment, the organic solvent is present in the mobile phase at a concentration of about 15% (v/v). In yet another embodiment, the organic solvent is present in the mobile phase at a concentration of about 20% (v/v). In certain embodiments, the concentration of the organic solvent in the mobile phase remains constant throughout the separation.

In some embodiments, the mobile phase comprises an elution salt, the concentration of which increases over the time period of the separation. An elution salt refers to an ionic compound resulting from a neutralization reaction of an acid and a base. A salt is typically comprised of an equal number of cations and anions so that the overall net charge of the salt is zero. As shown by the experimental results in Example 2 herein, the selection of elution salt can modulate the formation of the quadruplex structure and the ability to efficiently separate the quadruplex from single-stranded guanine-rich oligonucleotide and impurities. Suitable cations in the elution salt include, but are not limited to, sodium, potassium, ammonium, trimethylammonium, triethylammonium, lithium, calcium, and magnesium. In certain embodiments, the cation in the elution salt can be selected from sodium, potassium, ammonium, trimethylammonium, and triethylammonium. In some embodiments, the cation in the elution salt is sodium, potassium, or ammonium. In one embodiment, the cation in the elution salt is sodium. In another embodiment, the cation in the elution salt is potassium. Suitable anions in the elution salt include, but are not limited to, chloride, bromide, nitrate, nitrite, iodide, perchlorate, acetate, formate, phosphate, citrate, oxalate, and carbonate. The anion in the elution salt can, in some embodiments, be selected from chloride, bromide, nitrate, nitrite, iodide, perchlorate, acetate, and formate. In one particular embodiment, the anion in the elution salt is chloride. In another particular embodiment, the anion in the elution salt is bromide. Exemplary elution salts that can be included in the mobile phase include, but are not limited to, sodium chloride, sodium bromide, sodium nitrate, sodium nitrite, sodium acetate, sodium perchlorate, sodium iodide, sodium formate, potassium chloride, potassium bromide, potassium nitrate, potassium nitrite, potassium acetate, potassium perchlorate, potassium iodide, potassium formate, ammonium chloride, ammonium bromide, ammonium acetate, trimethylammonium chloride, trimethylammonium bromide, trimethylammonium acetate, triethylammonium chloride, triethylammonium bromide, and triethylammonium acetate. In certain embodiments, the mobile phase comprises an elution salt selected from sodium bromide, potassium bromide, ammonium bromide, sodium chloride, potassium chloride, and ammonium chloride. In one embodiment, the elution salt in the mobile phase is sodium bromide. In another embodiment, the elution salt in the mobile phase is potassium bromide. In another embodiment, the elution salt in the mobile phase is ammonium bromide.

During the separation, the concentration of the elution salt in the mobile phase is increased to disrupt the electrostatic interactions between the oligonucleotides/quadruplex and the monolithic anion exchange matrix. The increase in concentration of the elution salt in the mobile phase can be a concentration gradient of the elution salt, for example from 0 M to about 2 M, from 0 M to about 1 M, from 0 M to about 0.5 M, from about 0.5 M to about 1 M, or from about 0.5 M to about 2 M. In some embodiments, the gradient is a linear gradient where the concentration of elution salt in the mobile phase changes linearly over time. In other embodiments, the gradient is a step gradient where the concentration of elution salt in the mobile phase changes in discrete steps over time, where the elution salt concentration is constant at each step. Both linear and step gradients of the elution salt can be created by mixing different percentages of two buffers with different concentrations of the elution salt at different times.

By way of example, buffer A, which does not contain the elution salt, can be mixed with buffer B, which comprises 1 M of the elution salt, to create the gradients. By increasing the percentage of buffer B in the mixture with buffer A as a function of time allows the creation of a linear concentration gradient of the elution salt from 0 M to 1 M. Similarly, a step gradient can be created by mixing specific percentages of buffer A and buffer B at particular time points during the separation. In one embodiment, the increase in concentration of the elution salt in the mobile phase is a linear gradient from 0 M to 1 M. In another embodiment, the increase in concentration of the elution salt in the mobile phase is a step gradient from 0 M to 1 M. An exemplary step gradient for changing the concentration of the elution salt in the mobile phase over the course of the separation is described in the following table, where Buffer A does not contain any elution salt (i.e. 0 M) and Buffer B contains 1 M elution salt:

| Time (min) | % Buffer B |
|---|---|
| 0 | 0 |
| 15 | 55 |
| 25 | 55 |
| 30 | 100 |
| 32 | 100 |
| 32.1 | 0 |
| 37 | 0 |

Other possible gradients and methods for creating the gradients to increase the concentration of the elution salt in the mobile phase over the course of the separation are known to those of skill in the art.

In some embodiments of the methods of the invention, the mobile phase has a pH of about 7.0 to about 9.0 and comprises about 10 mM to about 200 mM buffer, about 1% (v/v) to about 50% (v/v) organic solvent, and an elution salt, wherein the concentration of the elution salt increases at a gradient of 0 M to about 2 M over time. In other embodiments, the mobile phase has a pH of about 7.5 to about 8.5 and comprises about 20 mM to about 100 mM buffer, about 1% (v/v) to about 20% (v/v) organic solvent, and an elution salt, wherein the concentration of the elution salt increases at a gradient of 0 M to about 1 M over time. For any of these mobile phase compositions, the buffer can be sodium phosphate or Tris hydrochloride, the organic solvent can be acetonitrile or methanol, and the elution salt can be sodium bromide, potassium bromide, or ammonium bromide. For instance, in certain embodiments, the mobile phase has a pH of about 7.0 to about 9.0 and comprises about 10 mM to about 200 mM sodium phosphate buffer, about 1% (v/v) to about 50% (v/v) acetonitrile, and sodium bromide, wherein the concentration of sodium bromide in the mobile phase increases at a gradient of 0 M to about 2 M over time. In some embodiments, the mobile phase has a pH of about 7.5 to about 8.5 and comprises about 20 mM to about 100 mM sodium phosphate buffer, about 1% (v/v) to about 20% (v/v) acetonitrile, and sodium bromide, wherein the concentration of sodium bromide in the mobile phase increases at a gradient of 0 M to about 1 M over time. In other embodiments, the mobile phase has a pH of about 8.0 to about 8.5 and comprises about 15 mM to about 25 mM sodium phosphate buffer, about 8% (v/v) to about 12% (v/v) acetonitrile, and sodium bromide, wherein the concentration of sodium bromide in the mobile phase increases at a gradient of 0 M to about 1 M over time. In one embodiment, the mobile phase has a pH of about 8.5 and comprises about 20 mM sodium phosphate buffer, about 10% (v/v) acetonitrile, and sodium bromide, wherein the concentration of sodium bromide in the mobile phase increases at a gradient of 0 M to about 1 M in a stepwise manner over time (i.e. a step gradient).

In certain embodiments of the methods, the mobile phase has a pH of about 7.0 to about 9.0 and comprises about 10 mM to about 200 mM sodium phosphate buffer, about 1% (v/v) to about 50% (v/v) methanol, and sodium bromide, wherein the concentration of sodium bromide in the mobile phase increases at a gradient of 0 M to about 2 M over time. In some embodiments, the mobile phase has a pH of about 7.5 to about 8.5 and comprises about 20 mM to about 100 mM sodium phosphate buffer, about 1% (v/v) to about 20% (v/v) methanol, and sodium bromide, wherein the concentration of sodium bromide in the mobile phase increases at a gradient of 0 M to about 1 M over time. In other embodiments, the mobile phase has a pH of about 8.0 to about 8.5 and comprises about 15 mM to about 25 mM sodium phosphate buffer, about 8% (v/v) to about 12% (v/v) methanol, and sodium bromide, wherein the concentration of sodium bromide in the mobile phase increases at a gradient of 0 M to about 1 M over time. In yet other embodiments, the mobile phase has a pH of about 7.0 to about 9.0 and comprises about 10 mM to about 200 mM Tris hydrochloride buffer, about 1% (v/v) to about 50% (v/v) methanol, and sodium bromide, wherein the concentration of sodium bromide in the mobile phase increases at a gradient of 0 M to about 2 M over time. In still other embodiments, mobile phase has a pH of about 7.5 to about 8.5 and comprises about 20 mM to about 100 mM Tris hydrochloride buffer, about 1% (v/v) to about 20% (v/v) methanol, and sodium bromide, wherein the concentration of sodium bromide in the mobile phase increases at a gradient of 0 M to about 1 M over time. In certain other embodiments, the mobile phase has a pH of about 7.0 to about 9.0 and comprises about 10 mM to about 200 mM Tris hydrochloride buffer, about 1% (v/v) to about 50% (v/v) acetonitrile, and sodium bromide, wherein the concentration of sodium bromide in the mobile phase increases at a gradient of 0 M to about 2 M over time. In still other embodiments, the mobile phase has a pH of about 7.5 to about 8.5 and comprises about 20 mM to about 100 mM Tris hydrochloride buffer, about 1% (v/v) to about 20% (v/v) acetonitrile, and sodium bromide, wherein the concentration of sodium bromide in the mobile phase increases at a gradient of 0 M to about 1 M over time. In any of the mobile phase buffers described above, potassium bromide or ammonium bromide can be used as the elution salt in place of sodium bromide.

Relative to particle-based stationary phases, monolithic stationary phases can accommodate high flow rates without compromising separation efficiency, thereby allowing faster separation times. Accordingly, the mobile phase can be applied to the monolithic anion exchange matrix at flow rates of 50 mL/min or higher depending on the size of the pores and size of the column. Typically, it is desirable to minimize the pressure required to drive the mobile phase through the monolithic matrix. The smaller the pore size, the greater the pressure required to drive the mobile phase through the monolithic matrix thereby necessitating slower flow rates. Conversely, larger pore sizes enable the use of higher flow rates while maintaining pressure at acceptable levels. In some embodiments, the monolithic anion exchange matrix employed in the methods of the invention has pore sizes of at least 500 nm, thereby allowing for flow rates of at least 50 mL/min or higher. For monolithic anion exchange matrices having larger pore sizes (e.g. greater than 1,000), the mobile phase can be applied at even higher flow rates, for example, at flow rates of at least 300 mL/min or higher. Thus, suitable flow rates at which the mobile phase can be applied to the monolithic anion exchange matrix include, but are not limited to, about 5 mL/min to about 500 mL/min, about 8 mL/min to about 100 mL/min, about 40 mL/min to about 400 mL/min, about 100 mL/min to about 300 mL/min, about 8 mL/min to about 60 mL/min, about 10 mL/min to about 20 mL/min, or about 8 mL/min to about 15 mL/min. In certain embodiments, the mobile phase is applied to the monolithic anion exchange matrix at a flow rate of about 8 mL/min to about 60 mL/min. In other embodiments, the mobile phase is applied to the monolithic anion exchange matrix at a flow rate of about 10 mL/min to about 20 mL/min. In still other embodiments, the mobile phase is applied to the monolithic anion exchange matrix at a flow rate of about 8 mL/min to about 15 mL/min. In one embodiment, the mobile phase is applied to the monolithic anion exchange matrix at a flow rate of about 10 mL/min. A person of ordinary skill in the art can determine other appropriate flow rates for the mobile phase depending on the pore size of the monolithic anion exchange matrix and the bed volume of the column to maintain acceptable pressure levels.

As the solution comprising the guanine-rich oligonucleotide, quadruplex structure formed from the guanine-rich oligonucleotide, and one or more impurities is moved through the monolithic anion exchange matrix with the mobile phase described herein, elution fractions are collected. The oligonucleotide content in the fractions can be monitored using UV absorption, e.g. at 260 nm. As shown by the chromatograms in the Figures (e.g. FIGS. 1A, 5A-C, and 6), when the monolithic anion exchange chromatography is operated according to the methods of the invention, the single-stranded guanine-rich oligonucleotide elutes from the monolithic anion exchange matrix prior to the quadruplex, thus enabling the collection of separate sets of fractions for the single-stranded guanine-rich oligonucleotide and for the quadruplex. As described in Example 2 and shown in FIGS. 5A-C and FIGS. 8A-B, the set of fractions containing the single-stranded oligonucleotide and the set of fractions containing the quadruplex are enriched for the single-stranded oligonucleotide and the quadruplex, respectively, and do not contain a significant amount of impurities, such as failure sequences. Samples from the elution fractions can be analyzed by gel electrophoresis, capillary electrophoresis, ion-pairing reversed phase liquid chromatography-mass spectrometry, analytical ion exchange chromatography, and/or native mass spectrometry to verify the enrichment of the fractions for the single-stranded guanine-rich oligonucleotide and the quadruplex.

The separation on the monolithic anion exchange matrix can be carried out at ambient temperature. For instance, in some embodiments, the separation on the monolithic anion exchange matrix is conducted at a temperature of about 15° C. to about 25° C. In other embodiments, the separation on the monolithic anion exchange matrix is conducted at a temperature of about 18° C. to about 22° C. In yet other embodiments, the separation on the monolithic anion exchange matrix is conducted at a temperature of about 20° C. to about 25° C. In certain embodiments, the separation on the monolithic anion exchange matrix is not conducted at a temperature above 35° C. As the formation of quadruplex secondary structures are induced and carefully controlled during the methods of the invention, the separation on the monolithic anion exchange matrix should be conducted at a temperature that would not denature or be incompatible with the formation of secondary structures. Accordingly, in some embodiments, the separation on the monolithic anion exchange matrix is conducted at a temperature of less than 35° C.

In certain embodiments of the methods of the invention, the elution fraction or set of elution fractions comprising the single-stranded guanine-rich oligonucleotide can be isolated and optionally pooled for further processing. For instance, the elution fraction(s) containing the guanine-rich oligonucleotide may be subject to one or more further purification steps, such as affinity separation (e.g. nucleic acid hybridization using sequence-specific reagents), additional ion exchange chromatography steps (e.g. using different stationary phases), reverse-phase chromatography, or size-exclusion chromatography (e.g. with a desalting column). In these and other embodiments, the elution fraction(s) containing the guanine-rich oligonucleotide may be subject to other reactions to modify the structure of the guanine-rich oligonucleotide. For example, in embodiments in which the guanine-rich oligonucleotide is a therapeutic molecule (e.g. antisense oligonucleotide) or component of a therapeutic molecule (e.g. double-stranded RNA interference agent, such as siRNA), the purified guanine-rich oligonucleotide in the elution fraction(s) may be subject to a conjugation reaction to covalently attach a targeting ligand, such as a carbohydrate-containing ligand, cholesterol, antibody, and the like, to the oligonucleotide. In other embodiments, the purified guanine-rich oligonucleotide in the elution fraction(s) may be encapsulated in exosomes, liposomes, or other type of lipid nanoparticle or formulated in a pharmaceutical composition with a pharmaceutically acceptable excipient for administration to patients for therapeutic purposes. In embodiments in which the guanine-rich oligonucleotide is a component of a double-stranded RNA interference agent (e.g. either the sense strand or antisense strand of an siRNA molecule), the purified guanine-rich oligonucleotide in the elution fraction(s) may be subject to an annealing reaction to hybridize the guanine-rich oligonucleotide with its complementary strand to form the double-strand RNA interference agent.

Figure 8A:
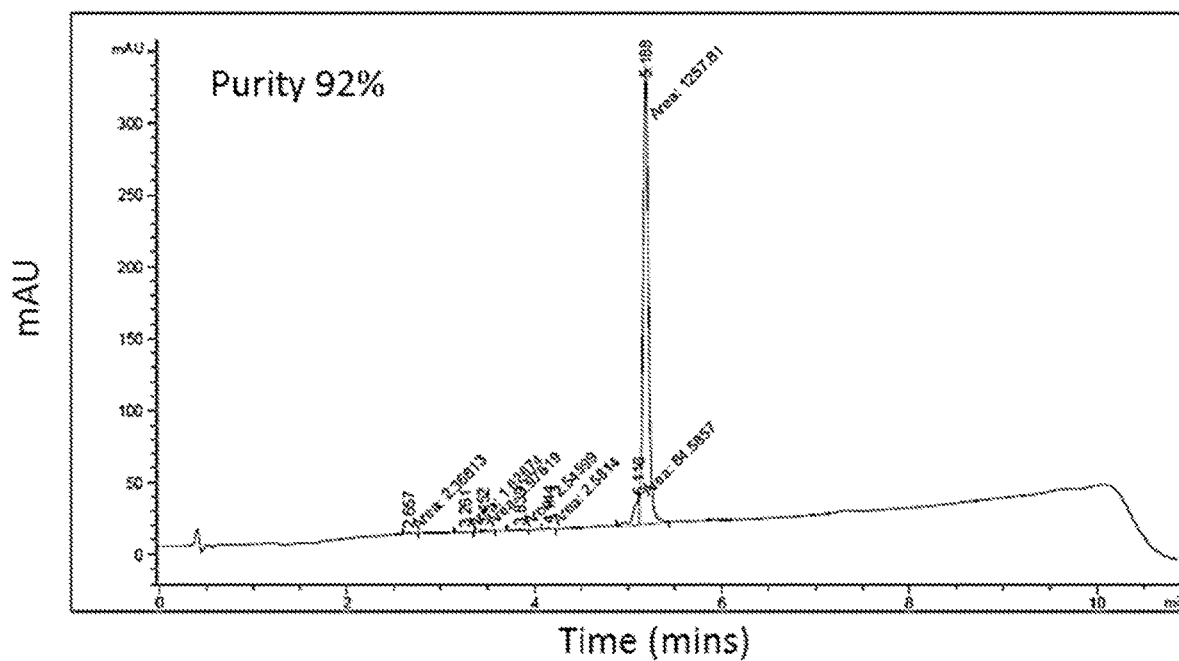
FIG. 8A is an ion-pairing reversed phase liquid chromatogram of collected fractions from a preparative anion exchange monolithic chromatography. Collected fractions comprising the quadruplex peak were combined, de-salted, and analyzed by ion-pairing reversed phase liquid chromatography using a Waters Xbridge BEH OST C18 column (2.1×50 mm, 2.5 µm) and a N,N-Diisopropylethylamine (DIEA), 50 mM Hexafluoro-2-propanol mobile phase with elution by an acetonitrile gradient. Detection at 260 nm absorbance.
Figure 8B:
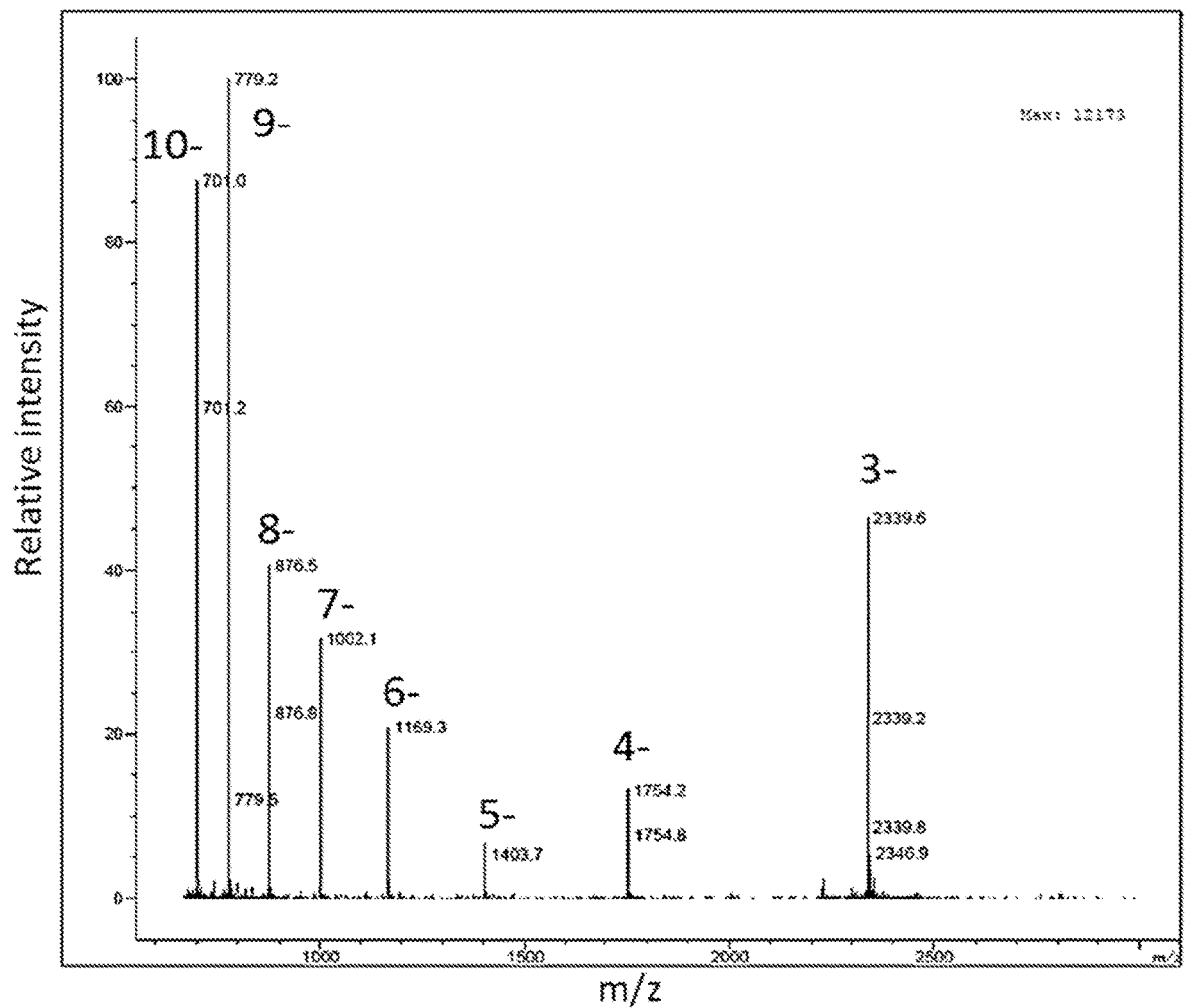
FIG. 8B is a mass spectrum of the single predominant peak from the ion-pairing reversed phase liquid chromatogram shown in FIG. 8A.

In some embodiments of the methods of the invention, the elution fraction or set of elution fractions comprising the quadruplex can be isolated and optionally pooled for further processing. The quadruplex can be used as an intact structure in subsequent assays or analyses to study and evaluate the function of the quadruplex structure in various systems. Alternatively, the elution fraction(s) containing the quadruplex can be subject to denaturing conditions to resolve the quadruplex into its component single-stranded guanine-rich oligonucleotide. As shown in FIGS. 8A-8B, the quadruplex is comprised predominantly of the single-strand oligonucleotide and does not significantly trap failure sequences and other impurities. Accordingly, by denaturing the quadruplex, highly purified preparations of the single-stranded guanine-rich oligonucleotide can be obtained. Thus, in certain embodiments, the elution fraction or set of elution fractions comprising the quadruplex are subject to denaturing conditions. The denaturing conditions can include denaturing of the quadruplex secondary structure by elevations in temperature, elevations in pH, exposure to chaotropic agents, exposure to organic agents, or combinations of any of these conditions.

In some embodiments, the quadruplex is denatured by heating the elution fraction(s) containing the quadruplex to an elevated temperature sufficient to disrupt the hydrogen bonding interactions among the guanine bases forming the G-quartets. For instance, the elution fractions(s) can be heated to a temperature from about 45° C. to about 95° C., from about 55° C. to about 85° C., or from about 65° C. to about 75° C. The temperature at which the quadruplex can be denatured can be adjusted based on the sequence and chemical modifications of the component oligonucleotides. Oligonucleotides that have a higher G C content or certain modified nucleosides have higher melting temperatures and thus quadruplex structures formed from such oligonucleotides may require higher temperatures to denature the quadruplex. In other embodiments, the quadruplex is denatured by increasing the pH of the elution fraction(s) comprising the quadruplex to strongly alkaline conditions. For example, the pH of the elution fraction(s) can be increased to a pH from about 9.5 to about 13, from about 10 to about 12, or from about 9.5 to about 11.5. In certain embodiments, the quadruplex is denatured by exposing the elution fraction (s) containing the quadruplex to a chaotropic agent. A chaotropic agent is a substance that disrupts the hydrogen bonding network among water molecules and can reduce the order in the structure of macromolecules by affecting intramolecular interactions mediated by non-covalent forces, such as hydrogen bonding, van der Waals forces, and hydrophobic interactions. Suitable chaotropic agents that can be used to denature the quadruplex include, but are not limited to, guanidinium chloride and other guanidinium salts, lithium acetate or lithium perchlorate, magnesium chloride, phenol, sodium dodecyl sulfate, urea, thiourea, and a thiocyanate salt (e.g. sodium thiocyanate, ammonium thiocyanate, or potassium thiocyanate). In one embodiment, the elution fraction(s) comprising the quadruplex are exposed to urea, for example at a concentration from about 1 M to about 8 M, to denature the quadruplex. Any other agents and methods that disrupt hydrogen bonding interactions known in the art can be used to denature the quadruplex to produce purified single-stranded guanine-rich oligonucleotides.

In embodiments in which the elution fraction or set of elution fractions comprising the quadruplex is subject to denaturing conditions to produce purified or enriched single-stranded guanine-rich oligonucleotide, the resulting solutions comprising the enriched single-stranded guanine-rich oligonucleotide can be subject to additional processing steps, such as any of the additional processing steps described above for the elution fraction(s) from the monolithic anion exchange matrix comprising the single-stranded guanine-rich oligonucleotide. For instance, the solutions comprising the enriched single-stranded guanine-rich oligonucleotides obtained from denaturing of the quadruplex may be subject to one or more purification steps, for example, to remove agents used in the denaturing step (e.g. chaotropic agents) or other process-related impurities (e.g. salt). In these and other embodiments, the solutions comprising the enriched single-stranded guanine-rich oligonucleotides obtained from denaturing of the quadruplex may be subject to other reactions, such as conjugation reactions to covalently link targeting ligands to the guanine-rich oligonucleotide or annealing reactions to hybridize the guanine-rich oligonucleotide to its complementary strand to produce double-stranded RNA interference agents (e.g. siRNA molecules). In some embodiments, the enriched single-stranded guanine-rich oligonucleotides obtained from denaturing of the quadruplex may be encapsulated in exosomes, liposomes, or other type of lipid nanoparticle or formulated in a pharmaceutical composition with a pharmaceutically acceptable excipient for administration to patients for therapeutic purposes.

In some embodiments, the methods of the invention can be performed iteratively to progressively enrich for the single-stranded guanine-rich oligonucleotide. For example, elution fractions comprising the single-strand guanine-rich oligonucleotide from the first run of the methods of the invention can be re-applied to the monolithic anion exchange matrix and separated again according to the methods of the invention. During the second and subsequent runs of the method, the guanine-rich oligonucleotide will again form the quadruplex structure, which can be isolated and denatured to obtain purified single-strand guanine-rich oligonucleotide. A solution comprising the single-stranded guanine-rich oligonucleotide can be run repeatedly in the methods of the invention until a preparation having the desired level of purity is achieved.

The methods of the invention provide substantially pure preparations of the guanine-rich oligonucleotide. For instance, in some embodiments, the purity of the guanine-rich oligonucleotide in elution fractions from the monolithic anion exchange matrix or in solutions comprising isolated and subsequently denatured quadruplex structures is at least 75%, at least 80%, at least 85%, at least 90%, at least 95%, at least 96%, at least 97%, at least 98%, or at least 99%. In certain embodiments, the purity of the guanine-rich oligonucleotide in elution fractions from the monolithic anion exchange matrix or in solutions obtained from denaturing the quadruplex is at least 85%. In other embodiments, the purity of the guanine-rich oligonucleotide in elution fractions from the monolithic anion exchange matrix or in solutions obtained from denaturing the quadruplex is at least 88%. In still other embodiments, the purity of the guanine-rich oligonucleotide in elution fractions from the monolithic anion exchange matrix or in solutions obtained from denaturing the quadruplex is at least 90%. Methods of detecting and quantitating oligonucleotides are known to those of skill in the art and can include ion-pairing reversed phase liquid chromatography-mass spectrometry methods and analytical ion exchange methods, such as those described in the examples.

The following examples, including the experiments conducted and the results achieved, are provided for illustrative purposes only and are not to be construed as limiting the scope of the appended claims.

EXAMPLES

Example 1. Purification of Guanine-Rich Oligonucleotides Using Ion Exchange Monolith Chromatography Ion exchange chromatography is a common technique for purifying natural and synthetic oligonucleotides. Anion-exchange columns, such as Source Q15 or Q30 (GE Healthcare), TSKgel SuperQ-5PW (Tosoh Bioscience), and DNA-Pac PA 200RS and DNAPac PA 100 (ThermoFisher Scientific), have been used to efficiently separate oligonucleotides, both on an analytical and preparative scale. See Amersham Biosciences, Strategies for large scale purification of synthetic oligonucleotides, Application note, 1-10; McGinnis et al., J Chromatogr B, Vol. 883-884:76-94, 2012; Noll et al., Nucleic Acid Ther, Vol. 21:383-393, 2011; and Thayer et al., J Chromatogr B, Vol. 878: 933-941, 2010. However, purification of oligonucleotides containing guanine-rich motifs that are capable of forming quadruplex secondary structures can be difficult or unachievable on such columns. This example describes the evaluation of anion exchange monolithic chromatography for separating guanine-rich oligonucleotides from quadruplex structures and impurities.

Initially, purification of a 21-mer, guanine-rich oligonucleotide using a conventional polymer bead-based anion exchange resin was compared to purification of the same oligonucleotide using an anion exchange monolithic column. The oligonucleotide (5'-UCGUAUAACAAUAAGGGGCUG-3' (SEQ ID NO: 1)) contained 2'-O-methyl- and 2'-fluoro-modified nucleotides and was synthesized on a solid support using phosphoramidite chemistry.

The two internucleotide linkages at the 5' and 3' terminal ends of the oligonucleotide were phosphorothioate internucleotide linkages, whereas all other internucleotide linkages were phosphodiester internucleotide linkages.

A solution comprising the oligonucleotide was separated either on a column packed with a polymer bead-based strong anion exchange resin (TSKgel SuperQ-5PW, Tosoh Bioscience) or a monolithic column comprising a strong anion exchange group (Convective Interaction Media (CIM)-QA 8 mL, BIA Separations). Specifications of the two types of columns are listed in Table 1 below.

TABLE 1

Anion-Exchange Column Specifications

| Column | Type of Support | Inner Diameter (mm) | Length (mm) | Particle size (μm) | Pore size (nm) | Dynamic binding capacity | Flow rate |
|---|---|---|---|---|---|---|---|
| TSKgel-SuperQ-5PW | Polymer bead | 21.5 | 150 | 13 μm | 100 | ~45 mg/mL | 1.5-8 mL/min |
| CIM-QA 8 mL | Monolith | 15 o.d.* 6.5 i.d. | 56 | N/A | 1300 | ~5.5 mg/mL | 8-60 mL/min |

*The CIM-QA-8 mL monolith column is tube shaped having an outer diameter (o.d.) and inner diameter (i.d.) as indicated. The monolith column has a bed volume of 8 mL.

1.2 mL of the solution containing the oligonucleotide was loaded on to each of the columns and was separated using a salt gradient, which was created by mixing Buffer A (20 mM $Na_2HPO_4$, 10% acetonitrile (v/v), pH 8.5) and Buffer B (20 mM $Na_2HPO_4$, 10% acetonitrile (v/v), 1 M NaBr, pH 8.5) as follows. For the TSKgel-SuperQ-5PW column, the buffers were applied to the column at a flow rate of 8 mL/min and the gradient conditions were: 0-20% Buffer B in 0-3 min, 20-65% Buffer B in 3-43 min, 65-80% Buffer B in 43-45 min, hold 80% B for 2 min, and 0% Buffer B at 48 min. For the CIM-QA column, the buffers were applied to the column at a flow rate of 10 mL/min and the gradient conditions were: 0-55% Buffer B in 0-15 min, 55% Buffer B at 15-25 min; 55-100% Buffer B at 25-30 min; 100% Buffer B at 30-32 min; and 0% Buffer B at 32.1-37 min. For both columns, the separations were conducted at ambient temperature. The fractions were collected and assayed for the 21-mer oligonucleotide or the quadruplex structure using analytical ion-exchange (DNAPac PA200 RS column, 4.6× 50 mm, 4 μm particle size) or ion-pairing reversed phase (Waters Xbridge BEH OST C18 column, 2.1×50 mm, 2.5 μm particle size) high performance liquid chromatography—mass spectrometry (HPLC-MS) methods. The results of the separation on each of the two columns are shown in FIG. 1.

The polymer bead-based chromatographic material (TSKgel-SuperQ-5PW column) has a ten-fold higher dynamic binding capacity as a result of a ten-fold reduction in pore size as compared to the monolithic chromatographic material (CIM-QA column)(Table 1). Therefore, it was anticipated that the TSKgel column would exhibit an overall higher retention for the 21-mer single strand oligonucleotide as well as the quadruplex. With the TSKgel column, a major peak was observed at ~38 mins and no distinct separation was observed between the single-stranded oligonucleotide and the quadruplex (dotted box in FIG. 1, B trace). In addition, all of the collected fractions had purities in the 61-74% range for the single-stranded oligonucleotide and the quadruplex. In contrast, the CIM-QA column allowed for separation of the single strand oligonucleotide from the quadruplex (FIG. 1, A trace). Complete elution of the quadruplex occurred in 30 mins on the CIM-QA column, as a result of higher flow rates, lower overall surface area of the monolith and substantially larger pore size of 1300 nm (FIG. 1, A trace).

The lack of separation between the single strand and the quadruplex on the TSKgel column could be attributed to the high surface area and the relatively small pore size of the column. The size of a 21-mer single strand oligoribonucleotide is in the range of 7 nm (Valiunas et al., J Physiol, Vol. 568: 459-468, 2005), whereas the pore size of the TSKgel column is 100 nm. Consequently, both the single strand and quadruplex would be able to penetrate the pores of the polymethacrylate particles of the stationary phase of the TSKgel column.

Recently, Shrestha and colleagues reported that the confinement effect can contribute to a rapid stabilization of the guanine-based quadruplex and enhance its formation (Shrestha et al., Nat. Nanotechnol, Vol. 12: 582-588, 2017). The authors demonstrated that quadruplex formation inside DNA origami nanocages was substantially more stable than in dilute solutions, with two orders of magnitude faster folding, and as the size of the cage decreased the mechanical and thermodynamic stability of the G-quadruplex increased (Shrestha et al., 2017). Analogously, without being bound by theory, the present inventors believe that the pores of the chromatographic stationary phase function as nanocages, inducing a similar confinement effect to enhance the folding and stabilization of the G-quadruplex. Accordingly, quadruplex folding should occur significantly faster on the TSK-gel column within the confined 100 nm pores, trapping impurities and failure sequences, before any separation can be achieved, which indeed appears to be the case as shown in the B trace in FIG. 1. In contrast, the larger pore sizes of the monolithic column would decrease the confinement effect, slowing down quadruplex assembly and promoting its separation away from the impurities/failure sequences and the single strand. The results shown in the A trace in FIG. 1 support this hypothesis as the quadruplex is able to be efficiently separated from the single strand on the monolithic column.

Next, to determine the capacity and throughput of the monolithic column to separate the single strand guanine-rich oligonucleotide from the quadruplex, various amounts of the oligonucleotide were loaded onto the column. Specifically, the oligonucleotide was loaded onto the monolithic column at amounts ranging from 10 mg to 50 mg and the separation was conducted using the conditions described above for the CIM-QA column. The fractions were collected and analyzed using analytical ion-exchange (DNAPac PA200 RS column, 4.6×50 mm, 4 µm particle size; 2 mL/min flow rate; temperature 70° C.) and ion-pairing reversed phase HPLC-MS (Waters Xbridge BEH OST C18 column, 2.1×50 mm, 2.5 µm particle size; 0.4 mL/min flow rate; temperature 60° C.) methods to ascertain purity of the fractions for the single strand oligonucleotide and the quadruplex.

Figure 2:
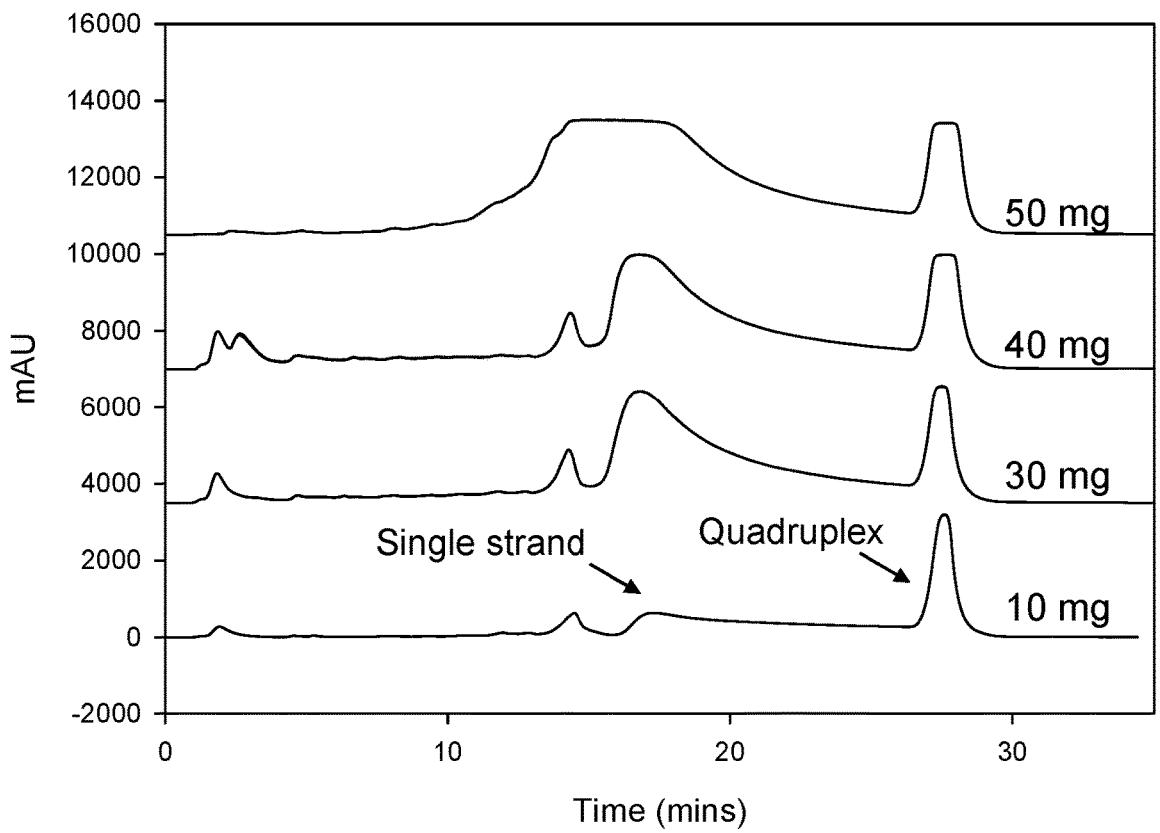
FIG. 2 shows preparative chromatograms of the separation of a guanine-rich 21-mer oligonucleotide at varying load amounts using an anion exchange monolithic column (CIM-QA-8 mL column). The oligonucleotide was loaded onto the column at 10 mg (400 µL), 30 mg (1200 µL), 40 mg (1600 µL) or 50 mg (2000 µL) and separated at a flow rate of 10 mL/min using a 20 mM $Na_2HPO_4$, 10% acetonitrile (v/v) mobile phase, pH 8.5 with elution by an increasing gradient of sodium bromide. Detection was by UV absorbance at 260 nm.
Figure 3:
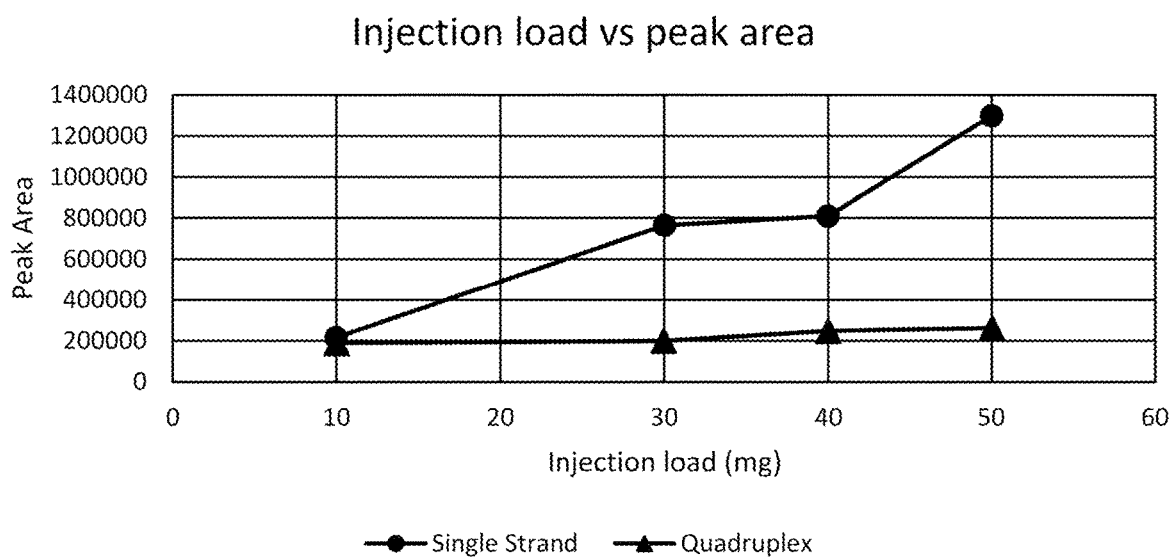
FIG. 3 is a line graph comparing injection load of a guanine-rich 21-mer oligonucleotide on an anion exchange monolithic column to the peak area for the single strand and quadruplex from the chromatograms shown in FIG. 2.

Preparative chromatograms of the separations are shown in FIG. 2. The results show that the highest load amount does not yield the best recovery and purity. In fact, at the larger load amounts of 40 mg and 50 mg the purity of the quadruplex was diminished. The 10 mg and 30 mg load amounts produced equivalent purity of the quadruplex, but the latter load amount afforded enhancement in the throughput. Thus, the optimal load amount for achieving the best purity of the quadruplex and throughput of the method was 30 mg. Increasing the injection load had a minimal effect on the peak area of the quadruplex, but instead significantly influenced single strand formation (FIG. 3). This result indicates that the monolithic surface is saturated for the quadruplex at ~ 40-50 mg loads, and with a 50 mg load amount, the single strand becomes the predominant species, displaying clear indication of overloading.

The results of the experiments described in this example demonstrate that a four-stranded quadruplex structure formed from short guanine-rich oligonucleotides can be separated efficiently from the single-strand oligonucleotide as well as impurities using an anion exchange monolithic column with large pore sizes. The large pore size of the monolithic column (~1.3 µm) and the unique surface of the monolith provides adequate accessible surface with which the quadruplex can interact, thereby enabling separation from the single-strand oligonucleotide, while providing short overall analysis time. The monolithic support provided better resolution between the single-strand oligonucleotide and quadruplex than the conventional polymer bead-based resin resulting in a higher overall purity of the quadruplex. The reduced confinement effect on the monolithic support induced slower quadruplex formation encouraging a better separation between the single strand and quadruplex. The quadruplex structure can then be isolated for further study or further denatured to obtain the purified single-strand oligonucleotide.

Example 2. Optimization of Mobile Phase Parameters to Modulate Quadruplex Formation To study factors that affect the retention, resolution and selectivity of the quadruplex, various mobile phase parameters were investigated. First, the effect of the type of cation employed in the mobile phase was evaluated. Previous studies have reported that various cations influence quadruplex stabilization and folding. See, e.g., Mergny et al., Nucleic Acids Res., Vol. 33: 81-94, 2005; Guo and Bartel, Science, Vol. 353(6306): aaf5371, 2016; Klejevskaja et al., Chem Commun (Camb), Vol. 52: 12454-12457, 2016; Olivas et al., Biochemistry, Vol. 34: 278-284, 1995; and Yuan et al., Mass Spectrom Rev, Vol. 30: 1121-1142, 2011. Ammonium, sodium, and potassium were evaluated as the counter cation in the elution salt in Buffer B.

Specifically, the mobile phase buffers were:

Buffer A: 20 mM $Na_2HPO_4$, 10% acetonitrile (v/v), pH 8.5

Buffer B1: 20 mM $Na_2HPO_4$, 10% acetonitrile (v/v), 1 M NaBr, pH 8.5

Buffer B2: 20 mM $Na_2HPO_4$, 10% acetonitrile (v/v), 1 M $NH_4Br$, pH 8.5

Buffer B3: 20 mM $Na_2HPO_4$, 10% acetonitrile (v/v), 1 M KBr, pH 8.5

1.2 mL of the solution containing the 21-mer guanine-rich oligonucleotide (SEQ ID NO: 1) was loaded on to a CIM-QA 8 mL anion exchange monolithic column and separated at ambient temperature at a flow rate of 10 mL/min using a salt gradient generated by mixing Buffer A and Buffer B1, B2, or B3 as follows:

| Time (min) | % Buffer B (B1, B2, or B3) |
|---|---|
| 0 | 0 |
| 15 | 55 |
| 25 | 55 |
| 30 | 100 |
| 32 | 100 |
| 32.1 | 0 |
| 37 | 0 |

Figure 4A:
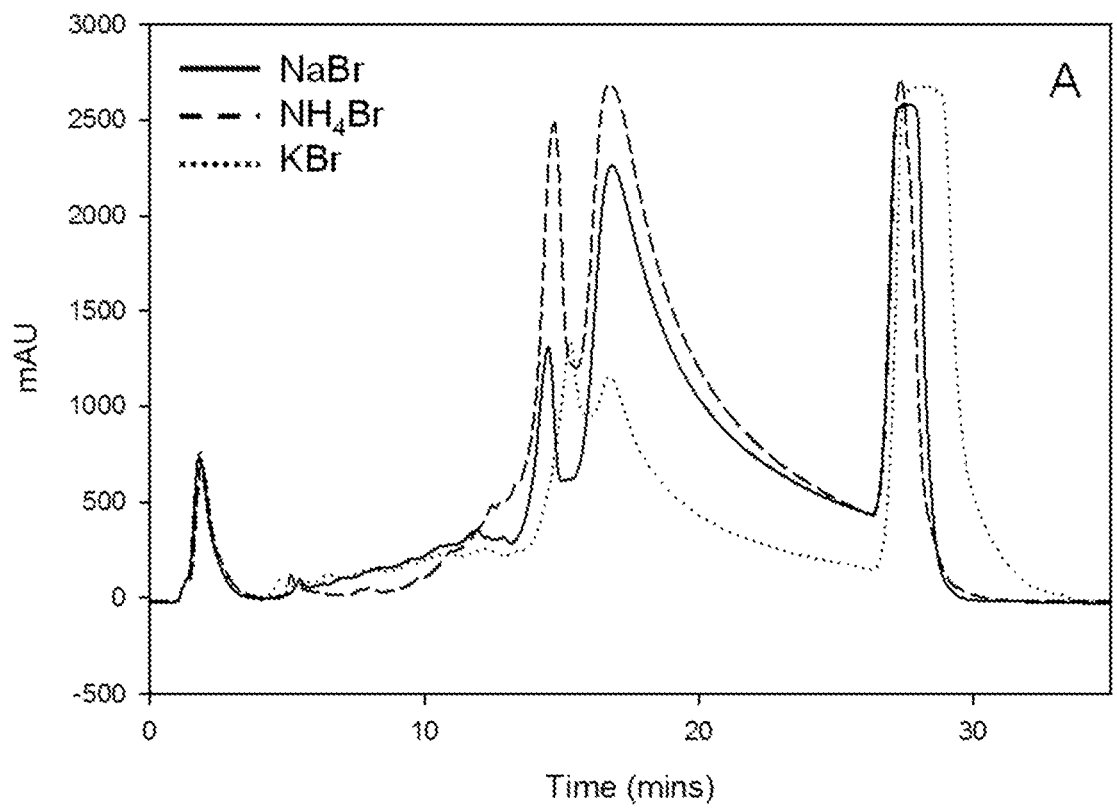
FIG. 4A depicts preparative chromatograms of the separation of a guanine-rich 21-mer oligonucleotide using an anion exchange monolithic column (CIM-QA-8 mL column) and different cations in the elution salt in the mobile phase. The oligonucleotide was loaded onto the column at 30 mg (1200 µL) and separated at a flow rate of 10 mL/min using a 20 mM $Na_2HPO_4$, 10% acetonitrile (v/v) mobile phase, pH 8.5 with elution by an increasing gradient of sodium bromide, ammonium bromide, or potassium bromide. Detection was by UV absorbance at 260 nm. The single-strand oligonucleotide elutes from the column at about 17.5 min, whereas the quadruplex elutes from the column at about 28 min.

FIG. 4A shows the preparative chromatograms for the separations using the different B buffers with the different counter cations. Although use of potassium as the counter cation favors quadruplex stabilization, it does not provide the highest purity of the quadruplex, because the quadruplex tends to trap failure sequences when purified using potassium as the counter cation.

Use of ammonium as the counter cation provides the least amount of quadruplex formation, whereas sodium as the counter cation affords the highest recovery as well as purity of the quadruplex. Thus, sodium was selected as the optimal counter-cation.

Different counter anions in the elution salt were also evaluated since these anions govern retention and selectivity of the negatively-charged oligonucleotides under ion-exchange conditions. Bromide and chloride were evaluated as the counter anion in the elution salt in Buffer B. The mobile phase buffers for this experiment were:

Buffer A: 20 mM $Na_2HPO_4$, 10% acetonitrile (v/v), pH 8.5

Buffer B1: 20 mM $Na_2HPO_4$, 10% acetonitrile (v/v), 1 M NaBr, pH 8.5

Buffer B2: 20 mM $Na_2HPO_4$, 10% acetonitrile (v/v), 1 M NaCl, pH 8.5

Figure 4B:
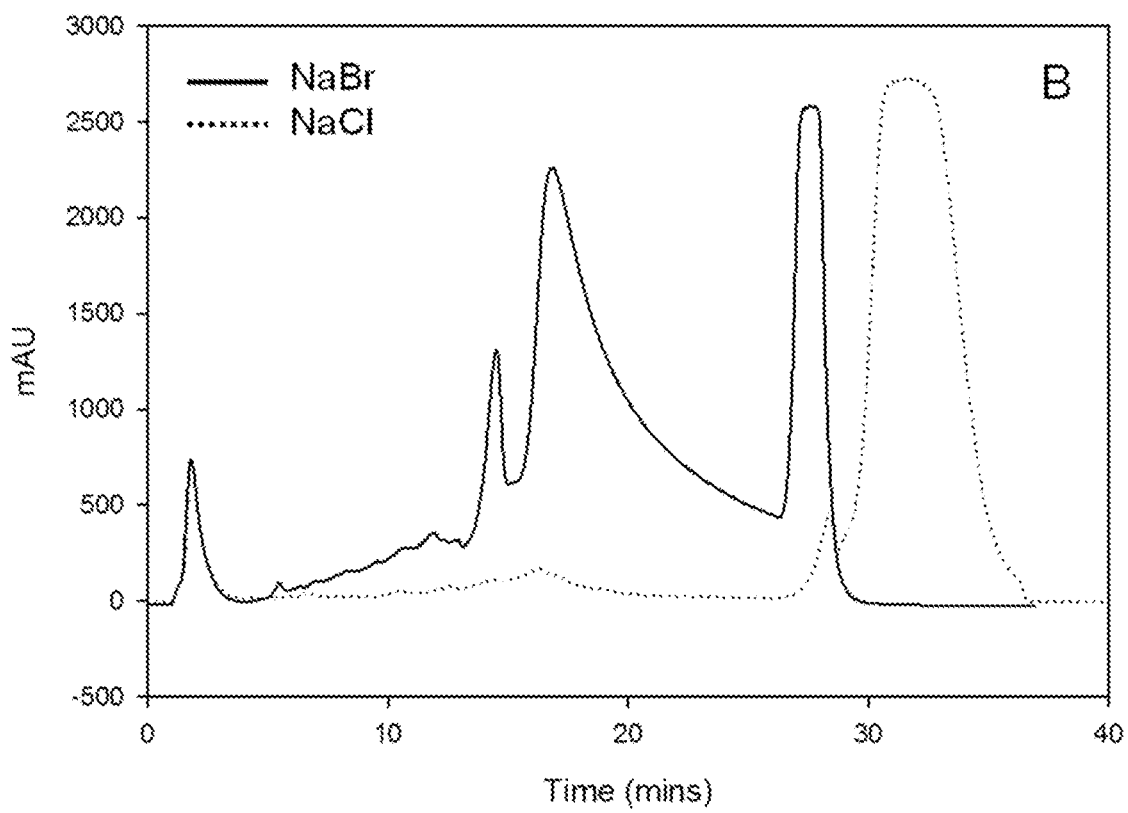
FIG. 4B depicts preparative chromatograms of the separation of a guanine-rich 21-mer oligonucleotide using an anion exchange monolithic column (CIM-QA-8 mL column) and different anions in the elution salt in the mobile phase. The oligonucleotide was loaded onto the column at 30 mg (1200 µL) and separated at a flow rate of 10 mL/min using a 20 mM $Na_2HPO_4$, 10% acetonitrile (v/v) mobile phase, pH 8.5 with elution by an increasing gradient of sodium bromide or sodium chloride. Detection was by UV absorbance at 260 nm.

1.2 mL of the solution containing the 21-mer guanine-rich oligonucleotide (SEQ ID NO: 1) was loaded on to a CIM-QA 8 mL anion exchange monolithic column and separated at ambient temperature at a flow rate of 10 mL/min using a salt gradient generated by mixing Buffer A and Buffer B1 or B2, according to the same gradient parameters described in the table immediately above for the counter cation experiment. FIG. 4B shows the resulting preparative chromatograms from this experiment. The presence of chloride in the mobile phase resulted in a longer retention time for the quadruplex and poorer separation between the single-strand oligonucleotide and the quadruplex. In contrast, the presence of bromide in the mobile phase resulted in a near baseline separation of the single-strand oligonucleotide and the quadruplex with a shorter overall analysis time.

High pH values are known to disrupt secondary interactions and thus possibly result in diminished quadruplex formation. Therefore, buffer pH was also investigated. The pH of the mobile phase buffers (buffer A: 20 mM $Na_2HPO_4$, 10% acetonitrile (v/v); buffer B: 20 mM $Na_2HPO_4$, 10% acetonitrile (v/v), 1 M NaBr) were adjusted to either pH 7.5 or pH 8.5. The two different mobile phase conditions resulted in near identical chromatograms despite the differences in pH (data not shown).

Based on the series of experiments evaluating the different mobile phase parameters, the optimal conditions for separating the single-strand guanine-rich oligonucleotide from the quadruplex were determined to be:

Column: CIM-QA 8 mL anion exchange monolithic column
Flow rate: 10 mL/min
Temperature: ambient
Injection volume: 1200 μL
Mobile phase:
　Buffer A: 20 mM $Na_2HPO_4$, 10% acetonitrile (v/v), pH 8.5
　Buffer B: 20 mM $Na_2HPO_4$, 10% acetonitrile (v/v), 1 M NaBr, pH 8.5
Step gradient conditions:

| Time (min) | % Buffer B |
| --- | --- |
| 0 | 0 |
| 15.0 | 55 |
| 25.0 | 55 |
| 30.0 | 100 |
| 32.0 | 100 |
| 32.1 | 0 |
| 37.0 | 0 |

The threshold for collection of fractions was set at 300 mAU. The purity of the fractions was confirmed using an ion-pairing reversed phase HPLC-MS method (Waters Xbridge BEH OST C18 column, 2.1×50 mm, 2.5 μm particle size; 0.4 mL/min flow rate; temperature 60° C.). The fractions collected for the quadruplex displayed purities in the range of 88-93%.

To confirm the presence of single-strand oligonucleotide and quadruplex in the different fractions, native mass spectrometry (MS) experiments were carried out on the relevant fractions following the preparative purification with the anion exchange monolithic column. 1.2 mL of the solution containing the 21-mer guanine-rich oligonucleotide (SEQ ID NO: 1) was loaded on to a CIM-QA 8 mL anion exchange monolithic column and separated at ambient temperature at a flow rate of 10 mL/min using a salt gradient, which was created by mixing Buffer A (20 mM $Na_2HPO_4$, 10% acetonitrile (v/v), pH 8.5) and Buffer B (20 mM $Na_2HPO_4$, 10% acetonitrile (v/v), 1 M $NH_4Br$, pH 8.5) as follows: 0-55% Buffer B in 0-15 min, 55% Buffer B at 15-25 min; 55-100% Buffer B at 25-30 min; 100% Buffer B at 30-32 min; and 0% Buffer B at 32.1-37 min. The threshold for fraction collection was set at 500 mAU. The fractions were desalted by size exclusion chromatography (HiPrep 26/10 desalting column; 26×100 mm, 90 μm particle size) and subject to native MS analysis. For the native MS analysis, samples were buffer exchanged into 200 mM ammonium acetate using a P6 spin column (BioRad, 732-6221) and introduced into the mass spectrometer using nESI gold coated glass needles (long thin wall, M956232AD1-S; Waters Corporation). The native-MS experiments were performed using the Synapt G1 Q-ToF instrument (Waters Corporation) in both positive and negative ionization modes. Basic instrument voltages and pressures were: Sample Cone 50V, Trap CE 20V, Trap Gas Xe at $1.0e^{-2}$ mBar.

FIG. 5A shows the resulting chromatogram from the preparative purification and FIGS. 5B and 5C show the native mass spectra for Fraction 25 and Fraction 50 (indicated by boxes in the preparative chromatogram), respectively. As evident from the mass spectrum in FIG. 5B, the earlier fraction 25 mostly contains the single-strand oligonucleotide with a molecular weight of 7,021 Da (+/−1 Da). Low levels of highly adducted quadruplex signal were also detected in fraction 25. Fraction 50 contains the quadruplex having a molecular weight of 28,118 Da (+/−8 Da) (FIG. 5C). The intact quadruplex was the primary species detected in this fraction. These results demonstrate that the anion exchange chromatographic method using the monolithic matrix can effectively purify the single-strand guanine-rich oligonucleotide and the quadruplex structure.

Figure 6:
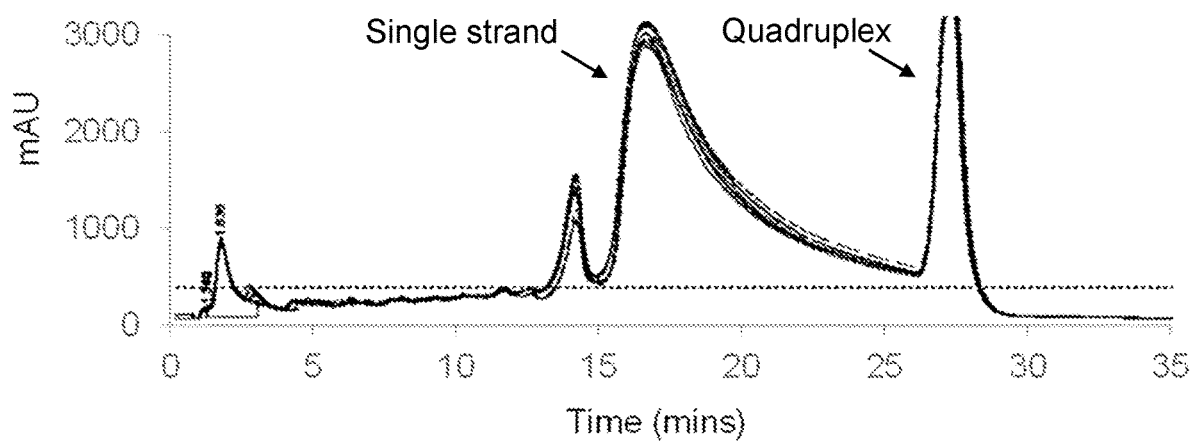
FIG. 6 shows overlaid preparative chromatograms from 24 separations of a guanine-rich 21-mer oligonucleotide using an anion exchange monolithic column (CIM-QA-8 mL column). The oligonucleotide was loaded onto the column at 30 mg (1200 µL) and separated at a flow rate of 10 mL/min using a 20 mM $Na_2HPO_4$, 10% acetonitrile (v/v) mobile phase, pH 8.5 with elution by an increasing gradient of sodium bromide. Detection was by UV absorbance at 260 nm. The single-strand oligonucleotide elutes from the column at about 17.5 min, whereas the quadruplex elutes from the column at about 28 min. The relative standard deviation (RSD) of retention time is less than 1%.
Figure 7A:
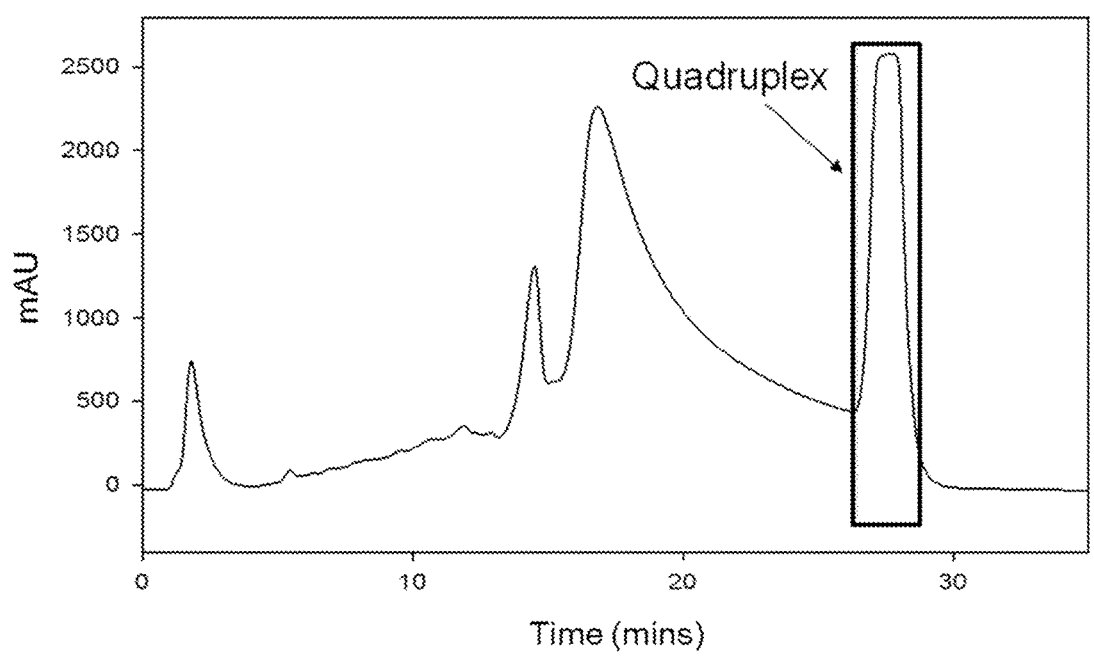
FIG. 7A depicts a preparative chromatogram of the separation of a guanine-rich 21-mer oligonucleotide using an anion exchange monolithic column (CIM-QA-8 mL column). The oligonucleotide was loaded onto the column at 30 mg (1200 µL) and separated at a flow rate of 10 mL/min using a 20 mM $Na_2HPO_4$, 10% acetonitrile (v/v) mobile phase, pH 8.5 with elution by an increasing gradient of sodium bromide. The fraction containing the peak corresponding to the quadruplex (indicated by the box) was analyzed by native mass spectrometry to determine purity.
Figure 7B:
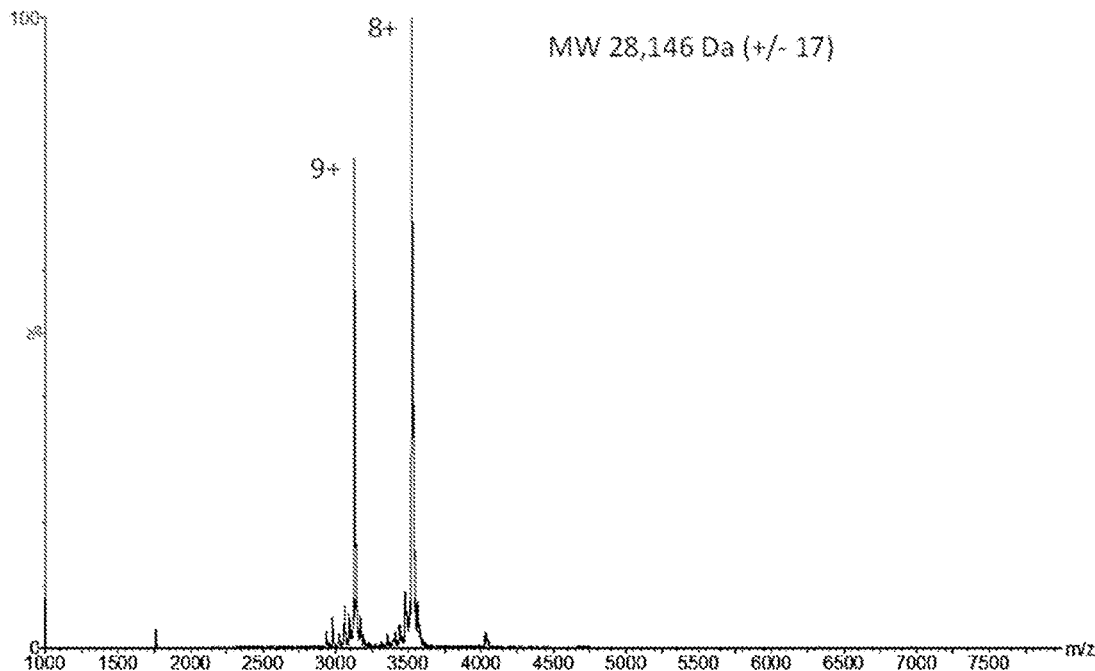
FIG. 7B is a native mass spectrum of the quadruplex fraction from the preparative chromatographic purification shown in FIG. 7A. Two primary peaks corresponding to a molecular weight of about 28 kDa are observed, which is the expected molecular weight for the intact quadruplex comprised of four strands of the guanine-rich oligonucleotide. The absence of other peaks indicates that the quadruplex fraction is pure.

To evaluate the variability of the purification method, the method was run 24 separate times with the guanine-rich oligonucleotide under the optimal mobile phase conditions. Specifically, 1.2 mL of the solution containing the 21-mer guanine-rich oligonucleotide (SEQ ID NO: 1) was loaded on to a CIM-QA 8 mL anion exchange monolithic column and separated at ambient temperature at a flow rate of 10 mL/min using a salt gradient, which was created by mixing Buffer A (20 mM $Na_2HPO_4$, 10% acetonitrile (v/v), pH 8.5) and Buffer B (20 mM $Na_2HPO_4$, 10% acetonitrile (v/v), 1 M NaBr, pH 8.5) as follows: 0-55% Buffer B in 0-15 min, 55% Buffer B at 15-25 min; 55-100% Buffer B at 25-30 min; 100% Buffer B at 30-32 min; and 0% Buffer B at 32.1-37 min. As shown in FIG. 6, the method produces excellent run-to-run repeatability with a relative standard deviation (RSD) of retention time less than 1%. Under these mobile phase conditions, the quadruplex is efficiently separated from the single-strand oligonucleotide (FIG. 7A). The identity of the quadruplex was confirmed by native MS with a signature corresponding to a molecular weight of 28,146 Da (+/−17 Da)(FIG. 7B). The quadruplex was the predominant species detected, indicating that the method can produce a purified intact quadruplex (FIG. 7B). The conditions for the native MS were the same as those described above except that $SF_6$ was used as the collision gas instead of Xe.

Three fractions containing the quadruplex peak from a single preparative purification were combined and desalted by size exclusion chromatography (HiPrep 26/10 desalting column; 26×100 mm, 90 μm particle size). The combined fractions were analyzed by an analytical ion-pairing reversed phase HPLC-MS method (Waters Xbridge BEH OST $C_{18}$ column, 2.1×50 mm, 2.5 μm particle size; 0.4 mL/min flow rate; temperature 60° C.), which results in the denaturing of the quadruplex, to determine the purity of the single-strand guanine-rich oligonucleotide in the fractions. As shown in FIG. 8A, the purity of the single-strand oligonucleotide in the combined fractions was 92%. The minor fronting of the peak was an impurity. The mass spectrum is shown in FIG. 8B and shows the ionization pattern expected for the single-strand guanine-rich oligonucleotide, suggesting that the quadruplex is comprised predominantly of the single-strand oligonucleotide and does not significantly trap failure sequences and other impurities.

Figure 8C:
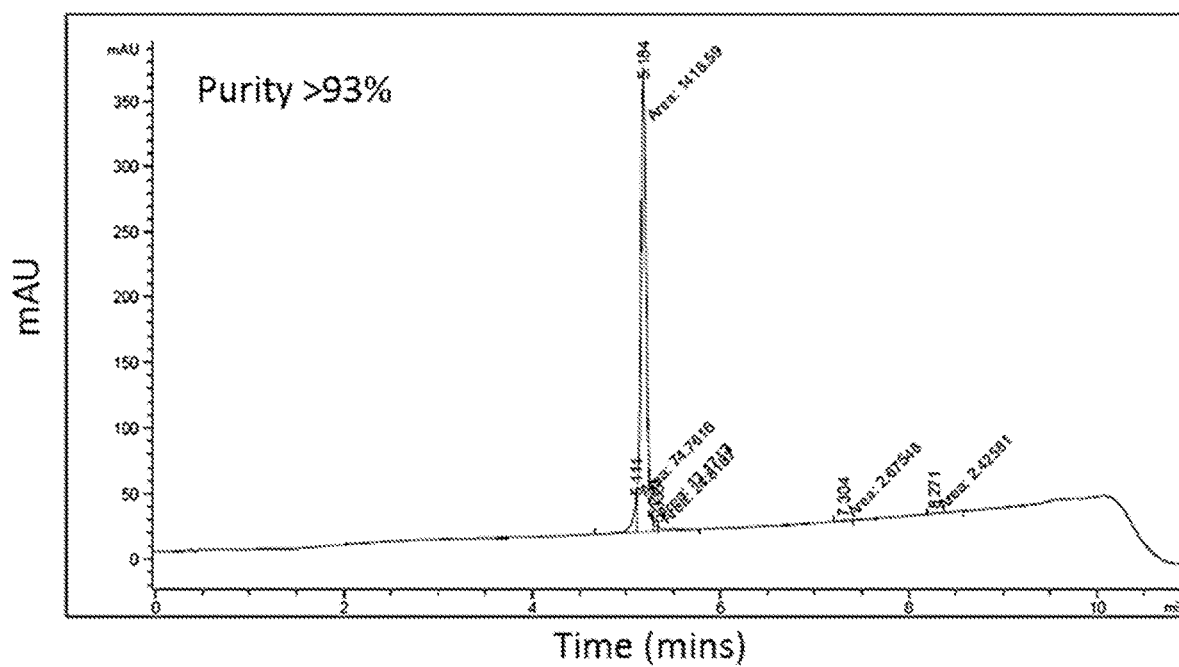
FIG. 8C is an ion-pairing reversed phase liquid chromatogram of a sample from a trityl-on purification of the single-strand guanine-rich oligonucleotide and is representative of purified preparations of the single-strand guanine-rich oligonucleotide. The sample was analyzed by ion-pairing reversed phase liquid chromatography using a Waters Xbridge BEH OST C18 column (2.1×50 mm, 2.5 µm) and a N,N-Diisopropylethylamine (DIEA), 50 mM Hexafluoro-2-propanol mobile phase with elution by an acetonitrile gradient. Detection at 260 nm absorbance.
Figure 8D:
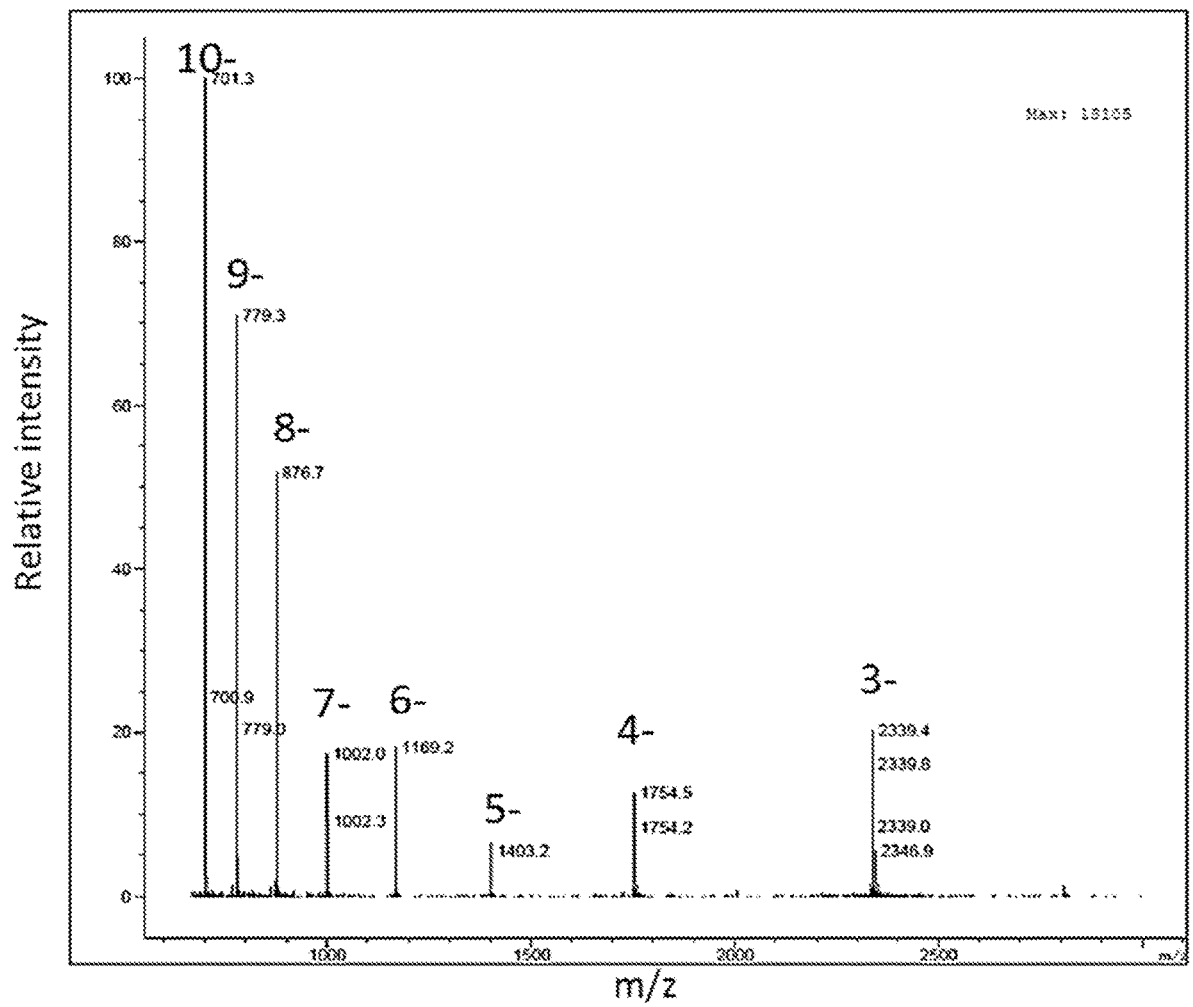
FIG. 8D is a mass spectrum of the single peak from the ion-pairing reversed phase liquid chromatogram shown in FIG. 8C.

For comparison purposes, the single-strand guanine-rich oligonucleotide was purified using a trityl-on purification method and analyzed by the analytical ion-pairing reversed phase HPLC-MS method described above. The trityl-on purification was conducted with a Kinetex EVO C18 column (30×250 mm, 5 μm) using a 0.1 M ammonium bicarbonate in water, pH 9.0 mobile phase and eluted with an acetonitrile gradient. The trityl-on purification yields single-strand oligonucleotide at a purity greater than 93%. The ion-pairing reversed phase liquid chromatogram for the trityl-on purified single-strand oligonucleotide is shown in FIG. 8C and the mass spectrum is shown in FIG. 8D. The chromatogram for the quadruplex shown in FIG. 8A is nearly identical to the chromatogram for the single-strand oligonucleotide shown in FIG. 8C, demonstrating that under the denaturing conditions of the analytical ion-pairing reversed phase HPLC the quadruplex is resolved into its component single-strand guanine-rich oligonucleotides, and little to no impurities are present. The mass spectrum for the denatured quadruplex sample shown in FIG. 8B is similar to the mass spectrum for the single-strand oligonucleotide shown in FIG. 8D showing that the quadruplex is predominantly comprised of the single-strand oligonucleotides and does not trap impurities.

The monolithic anion exchange preparative method resulted in greater than 200 mg of the purified quadruplex. This method can be readily scaled up by employing larger volume monolithic columns, such as the CIM-QA-80 mL and CIM-QA-800 mL columns available from BIA Separations.

A summary of the parameters for the analytical chromatographic methods and the desalting method described in this example and Example 1 are listed below:

Analytical Ion-Exchange Method
Column: DNA Pac PA 200 RS (4.6×50 mm, 4 μm)
Flow rate: 2 mL/min
Temperature: 70° C.
Mobile phase:
    Buffer A: 20 mM $Na_2HPO_4$, 10% acetonitrile, pH 8.5
    Buffer B: 20 mM $Na_2HPO_4$, 10% acetonitrile, 1 M NaBr, pH 8.5
Gradient purification conditions:

| Time (min) | % Buffer B |
|---|---|
| 0 | 25 |
| 3.5 | 65 |
| 3.7 | 25 |
| 4.6 | 25 |

Detection: Diode Array Detector at 260 nm

Analytical Ion-Pairing Reversed Phase Liquid Chromatography-Mass Spectrometry Method
Column: Waters Xbridge BEH OST C18 (2.1×50 mm, 2.5 μm)
Flow rate: 0.4 mL/min
Temperature: 60° C.
Mobile phase:
    Buffer A: 15.7 mM N,N-Diisopropylethylamine (DIEA), 50 mM Hexafluoro-2-propanol (HFIP) in water
    Buffer B: 15.7 mM DIEA, 50 mM HFIP in water:acetonitrile (50:50)
Gradient purification conditions:

| Time (min) | % Buffer B |
|---|---|
| 0 | 10 |
| 9.0 | 40 |
| 9.1 | 10 |
| 11.0 | 10 |

Detection: Diode Array Detector at 260 nm, followed by mass spectrometry

Desalting (Size Exclusion Chromatography)
Column: HiPrep 26/10 Desalting column (26×100 mm, 90 μm)
Mobile phase: 80:20 water:ethanol
Flow rate=10 mL/min All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. A method for separating a guanine-rich oligonucleotide from a quadruplex structure formed from the guanine-rich oligonucleotide, comprising:
contacting a solution comprising the guanine-rich oligonucleotide with a monolithic anion exchange matrix;
passing a mobile phase through the monolithic anion exchange matrix, wherein the mobile phase has a pH of about 7.0 to about 9.0 and comprises a buffer, an organic solvent, and an elution salt, wherein the concentration of the elution salt increases over time; and
collecting elution fractions from the monolithic anion exchange matrix, wherein the guanine-rich oligonucleotide is eluted in one set of elution fractions and a quadruplex formed from the guanine-rich oligonucleotide is eluted in another set of elution fractions, thereby separating the oligonucleotide from the quadruplex.

2. The method of claim 1, further comprising:
(a) isolating the set of elution fractions comprising the guanine-rich oligonucleotide and/or
(b) isolating the set of elution fractions comprising the quadruplex.

3. The method of claim 2, further comprising subjecting the fractions comprising the quadruplex to denaturing conditions, thereby producing purified single-strand guanine-rich oligonucleotide.

4. The method of claim 3, wherein the denaturing conditions comprise:
(a) heating the fractions comprising the quadruplex to a temperature from about 45° C. to about 95° C.;
(b) increasing the pH of the fractions comprising the quadruplex to a pH from about 9.5 to about 13; or
(c) exposing the fractions comprising the quadruplex to a chaotropic agent.

5. The method of claim 1, wherein the monolithic anion exchange matrix comprises a functional group selected from a quaternary amine, a polyethylenimine, a diethylaminomethyl, a diethylaminoethyl, a dimethylaminopropyl, an ethylendiamino, or a polyallylamine.

6. The method of claim 1, wherein the monolithic anion exchange matrix has a pore size of at least 200 nm.

7. The method of claim 1, wherein the monolithic anion exchange matrix has a pore size from about 500 nm to about 2,000 nm.

8. The method of claim 1, wherein the buffer is sodium phosphate, Tris hydrochloride, HEPES, or MOPS.

9. The method of claim 1, wherein the organic solvent is acetonitrile, methanol, propanol, isopropanol, ethanol, butanol, tetrahydrofuran, or acetone.

10. The method of claim 1, wherein the elution salt is sodium bromide, potassium bromide, ammonium bromide, sodium chloride, potassium chloride, or ammonium chloride.

11. The method of claim 1, wherein the increase in concentration of the elution salt in the mobile phase is a gradient from 0 M to 1 M.

12. The method of claim 1, wherein the mobile phase has a pH of about 7.5 to about 8.5.

13. The method of claim 1, wherein the mobile phase has a pH of about 7.5 to about 8.5 and comprises about 20 mM to about 100 mM sodium phosphate buffer, about 1% (v/v) to about 20% (v/v) acetonitrile, and sodium bromide, wherein the concentration of sodium bromide increases at a gradient of 0 M to 1 M over time.

14. The method of claim 13, wherein the mobile phase has a pH of about 8.5 and comprises about 20 mM sodium phosphate buffer, about 10% (v/v) acetonitrile, and sodium bromide, wherein the concentration of sodium bromide increases at a step gradient of 0 M to 1 M over time.

15. The method of claim 1, wherein the guanine-rich oligonucleotide comprises a nucleobase sequence of at least four consecutive guanine bases.

16. The method of claim 1, wherein the guanine-rich oligonucleotide is:
(a) an antisense oligonucleotide, wherein the antisense oligonucleotide comprises a nucleobase sequence complementary to a region of a target gene sequence having at least four consecutive cytosine bases;
(b) an antisense strand of an siRNA, wherein the antisense strand comprises a nucleobase sequence complementary to a region of a target gene sequence having at least four consecutive cytosine bases; or
(c) a sense strand of an siRNA, wherein the sense strand comprises a nucleobase sequence identical to a region of a target gene sequence having at least four consecutive guanine bases.

17. The method of claim 1, wherein the guanine-rich oligonucleotide comprises at least one modified nucleotide.

18. The method of claim 17, wherein the modified nucleotide is a 2'-fluoro modified nucleotide, a 2'-O-methyl modified nucleotide, a 2'-O-methoxyethyl modified nucleotide, a 2'-O-allyl modified nucleotide, a bicyclic nucleic acid (BNA), or combinations thereof.

19. The method of claim 1, wherein the guanine-rich oligonucleotide comprises at least one phosphorothioate internucleotide linkage.

20. The method of claim 1, where the guanine-rich oligonucleotide is about 12 nucleotides in length to about 100 nucleotides in length.

21. The method of claim 20, where the guanine-rich oligonucleotide is about 15 nucleotides in length to about 30 nucleotides in length.

22. A method for purifying a guanine-rich oligonucleotide capable of forming a quadruplex structure from one or more impurities, comprising:
contacting a solution comprising the oligonucleotide and one or more impurities with a monolithic anion exchange matrix;
passing a mobile phase through the monolithic anion exchange matrix, wherein the mobile phase has a pH of about 7.0 to about 9.0 and comprises a buffer, an organic solvent, and an elution salt, wherein the concentration of the elution salt increases over time; and
collecting elution fractions from the monolithic anion exchange matrix, wherein one or more impurities are eluted in a first set of elution fractions, the guanine-rich oligonucleotide is eluted in a second set of elution fractions, and a quadruplex structure formed from the guanine-rich oligonucleotide is eluted in a third set of elution fractions, thereby separating the oligonucleotide from the impurities.

23. The method of claim 22, wherein said one or more impurities comprises one or more failure sequences.

24. The method of claim 22, further comprising:
(a) isolating the second set of elution fractions comprising the guanine-rich oligonucleotide; and/or
(b) isolating the third set of elution fractions comprising the quadruplex.

25. The method of claim 24, further comprising subjecting the fractions comprising the quadruplex to denaturing conditions, thereby producing purified single-strand guanine-rich oligonucleotide.

26. The method of claim 25, wherein the denaturing conditions comprise:
(a) heating the fractions comprising the quadruplex to a temperature from about 45° C. to about 95° C.;
(b) increasing the pH of the fractions comprising the quadruplex to a pH from about 9.5 to about 13; or
(c) exposing the fractions comprising the quadruplex to a chaotropic agent.

27. The method of claim 22, wherein the monolithic anion exchange matrix comprises a functional group selected from a quaternary amine, a polyethylenimine, a diethylaminomethyl, a diethylaminoethyl, a dimethylaminopropyl, an ethylendiamino, or a polyallylamine.

28. The method of claim 22, wherein the monolithic anion exchange matrix has a pore size of at least 200 nm.

29. The method of claim 22, wherein the monolithic anion exchange matrix has a pore size from about 500 nm to about 2,000 nm.

30. The method of claim 22, wherein the buffer is sodium phosphate, Tris hydrochloride, HEPES, or MOPS.

31. The method of claim 22, wherein the organic solvent is acetonitrile, methanol, propanol, isopropanol, ethanol, butanol, tetrahydrofuran, or acetone.

32. The method of claim 22, wherein the elution salt is sodium bromide, potassium bromide, ammonium bromide, sodium chloride, potassium chloride, or ammonium chloride.

33. The method of claim 22, wherein the increase in concentration of the elution salt in the mobile phase is a gradient from 0 M to 1 M.

34. The method of claim 22, wherein the mobile phase has a pH of about 7.5 to about 8.5.

35. The method of claim 22, wherein the mobile phase has a pH of about 7.5 to about 8.5 and comprises about 20 mM to about 100 mM sodium phosphate buffer, about 1% (v/v) to about 20% (v/v) acetonitrile, and sodium bromide, wherein the concentration of sodium bromide increases at a gradient of 0 M to 1 M over time.

36. The method of claim 35, wherein the mobile phase has a pH of about 8.5 and comprises about 20 mM sodium phosphate buffer, about 10% (v/v) acetonitrile, and sodium bromide, wherein the concentration of sodium bromide increases at a step gradient of 0 M to 1 M over time.

37. The method of claim 22, wherein the guanine-rich oligonucleotide comprises a nucleobase sequence of at least four consecutive guanine bases.

38. The method of claim 22, wherein the guanine-rich oligonucleotide is:
(a) an antisense oligonucleotide, wherein the antisense oligonucleotide comprises a nucleobase sequence complementary to a region of a target gene sequence having at least four consecutive cytosine bases;
(b) an antisense strand of an siRNA, wherein the antisense strand comprises a nucleobase sequence complementary to a region of a target gene sequence having at least four consecutive cytosine bases; or
(c) a sense strand of an siRNA, wherein the sense strand comprises a nucleobase sequence identical to a region of a target gene sequence having at least four consecutive guanine bases.

39. The method of claim 22, wherein the guanine-rich oligonucleotide comprises at least one modified nucleotide.

40. The method of claim 39, wherein the modified nucleotide is a 2'-fluoro modified nucleotide, a 2'-O-methyl modified nucleotide, a 2'-O-methoxyethyl modified nucleotide, a 2'-O-allyl modified nucleotide, a bicyclic nucleic acid (BNA), or combinations thereof.

41. The method of claim 22, wherein the guanine-rich oligonucleotide comprises at least one phosphorothioate internucleotide linkage.

42. The method of claim 22, where the guanine-rich oligonucleotide is about 12 nucleotides in length to about 100 nucleotides in length.

43. The method of claim 42, where the guanine-rich oligonucleotide is about 15 nucleotides in length to about 30 nucleotides in length.

* * * * *